United States Patent
Mullaney

(10) Patent No.: US 8,388,619 B2
(45) Date of Patent: Mar. 5, 2013

(54) UNILATERAL FIXATOR

(75) Inventor: Michael W. Mullaney, Kinnelon, NJ (US)

(73) Assignee: SixFix Inc., Memphis, TN (US)

( * ) Notice: Subject to any disclaimer, the term of this patent is extended or adjusted under 35 U.S.C. 154(b) by 1353 days.

(21) Appl. No.: 11/841,091

(22) Filed: Aug. 20, 2007

(65) Prior Publication Data

US 2007/0282338 A1 Dec. 6, 2007

Related U.S. Application Data

(63) Continuation of application No. 10/664,769, filed on Sep. 17, 2003, now Pat. No. 7,282,052.

(60) Provisional application No. 60/411,291, filed on Sep. 17, 2002, provisional application No. 60/426,439, filed on Nov. 14, 2002.

(51) Int. Cl.
*A61B 17/56* (2006.01)

(52) U.S. Cl. .......................................................... 606/59

(58) Field of Classification Search .................. 606/53, 606/54, 57, 58, 59, 60, 246, 258, 86 R, 105; 403/109.1, 359.1
See application file for complete search history.

(56) References Cited

U.S. PATENT DOCUMENTS

| | | |
|---|---|---|
| 2,250,417 A | 7/1941 | Ettinger |
| 3,727,610 A | 4/1973 | Riniker |
| 4,308,863 A | 1/1982 | Fischer |
| 4,375,814 A | 3/1983 | Gourlandt |
| 4,483,334 A | 11/1984 | Murray |
| 4,502,473 A | 3/1985 | Harris et al. |
| 4,570,625 A | 2/1986 | Harris et al. |
| 4,621,627 A | 11/1986 | De Bastiani et al. |
| 4,628,919 A | 12/1986 | Clyburn |
| 4,730,608 A | 3/1988 | Schlein |
| 4,895,141 A | 1/1990 | Koeneman et al. |
| 4,922,896 A | 5/1990 | Agee et al. |
| 4,973,331 A | 11/1990 | Pursley et al. |
| 4,991,579 A | 2/1991 | Allen |
| 5,019,077 A | 5/1991 | De Bastiani et al. |
| 5,074,866 A | 12/1991 | Sherman et al. |
| 5,160,335 A | 11/1992 | Wagenknecht |

(Continued)

FOREIGN PATENT DOCUMENTS

| | | |
|---|---|---|
| DE | 10129942 | 2/2002 |
| EP | 0314021 | 5/1989 |

(Continued)

OTHER PUBLICATIONS

European Patent Office, Communication transmitting European search report dated Jul. 28, 2010, Application No. 03811627.3-2310/1567046 PCT/US0336590, 5 pages.

(Continued)

*Primary Examiner* — Eduardo C Robert
*Assistant Examiner* — David Comstock
(74) *Attorney, Agent, or Firm* — Haynes and Boone, LLP

(57) ABSTRACT

A unilateral fixator for adjustment of a first bone portion relative to a second bone portion. The fixator includes a telescopically adjustable strut having first and second ends and a strut axis, and first and second compound joints. The first compound joint is coupled to the first end of the strut and to a first bone clamp, and includes a first gear mechanism controlling linear and rotational motion of the first bone clamp relative to first and second axes while the first bone clamp is engaged with the first bone portion. The first and second axes are generally orthogonal to one another and to the strut axis. The second compound joint is coupled to the second end of the strut and to a second bone clamp and includes a second gear mechanism controlling linear and rotational adjustment of the second bone clamp. The first compound movable joints can rotate about the strut axis.

23 Claims, 29 Drawing Sheets

U.S. PATENT DOCUMENTS

Figure 1:
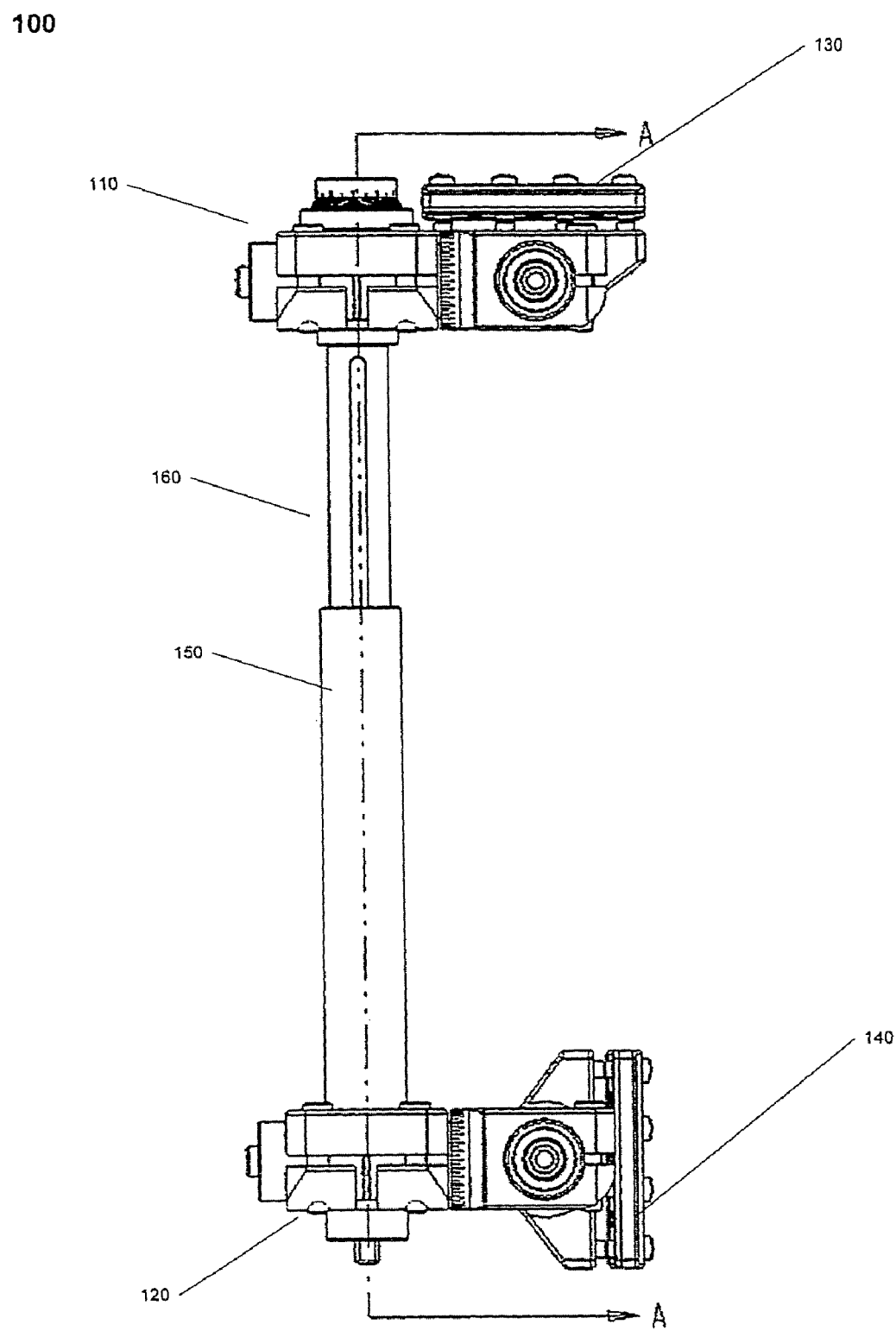

| | | | |
|---|---|---|---|
| 5,207,676 A | 5/1993 | Canadell et al. |
| 5,314,426 A | 5/1994 | Pohl et al. |
| 5,393,161 A | 2/1995 | Mata et al. |
| 5,429,637 A | 7/1995 | Hardy |
| 5,437,667 A | 8/1995 | Papierski et al. |
| 5,454,810 A | 10/1995 | Pohl et al. |
| 5,501,684 A | 3/1996 | Schlapfer et al. |
| 5,545,162 A | 8/1996 | Huebner |
| 5,601,551 A | 2/1997 | Taylor et al. |
| 5,653,707 A | 8/1997 | Taylor et al. |
| 5,658,283 A | 8/1997 | Huebner |
| 5,662,651 A | 9/1997 | Tornier et al. |
| 5,683,389 A | 11/1997 | Orsak |
| 5,688,271 A | 11/1997 | Faccioli et al. |
| 5,690,633 A | 11/1997 | Taylor et al. |
| 5,702,389 A | 12/1997 | Taylor et al. |
| 5,713,357 A | 2/1998 | Meulenbrugge et al. |
| 5,728,095 A | 3/1998 | Taylor et al. |
| 5,738,684 A | 4/1998 | Thomas et al. |
| 5,746,741 A | 5/1998 | Kraus et al. |
| 5,752,954 A | 5/1998 | Mata et al. |
| 5,776,132 A | 7/1998 | Blyakher |
| 5,788,695 A | 8/1998 | Richardson |
| 5,803,924 A | 9/1998 | Oni et al. |
| 5,843,081 A | 12/1998 | Richardson |
| 5,846,245 A | 12/1998 | McCarthy et al. |
| 5,891,144 A | 4/1999 | Mata et al. |
| 5,897,555 A | 4/1999 | Clyburn et al. |
| 5,928,230 A | 7/1999 | Tosic |
| 5,941,879 A | 8/1999 | Walulik et al. |
| 5,944,719 A | 8/1999 | Leban |
| 5,951,475 A | 9/1999 | Gueziec et al. |
| 5,951,556 A | 9/1999 | Faccioli et al. |
| 5,961,515 A | 10/1999 | Taylor et al. |
| 5,971,984 A | 10/1999 | Taylor et al. |
| 5,976,133 A | 11/1999 | Kraus et al. |
| 5,976,134 A | 11/1999 | Huebner |
| 6,017,341 A | 1/2000 | Windhagen et al. |
| 6,023,850 A | 2/2000 | Trapet |
| 6,030,386 A | 2/2000 | Taylor et al. |
| 6,036,691 A | 3/2000 | Richardson |
| 6,056,748 A | 5/2000 | Weiner |
| 6,080,153 A | 6/2000 | Mata et al. |
| 6,102,911 A | 8/2000 | Faccioli et al. |
| 6,129,727 A | 10/2000 | Austin et al. |
| 6,146,390 A | 11/2000 | Heilbrun et al. |
| 6,162,224 A | 12/2000 | Huebner |
| 6,171,308 B1 | 1/2001 | Bailey et al. |
| 6,171,309 B1 | 1/2001 | Huebner |
| 6,176,860 B1 | 1/2001 | Howard |
| 6,200,317 B1 | 3/2001 | Aalsma et al. |
| 6,245,071 B1 | 6/2001 | Pierson |
| 6,277,118 B1 | 8/2001 | Grant et al. |
| 6,277,119 B1 | 8/2001 | Walulik et al. |
| 6,340,361 B1 | 1/2002 | Kraus et al. |
| 6,348,053 B1 | 2/2002 | Cachia |
| 6,461,358 B1 | 10/2002 | Faccioli et al. |
| 6,491,694 B1 | 12/2002 | Orsak |
| 6,514,254 B1 | 2/2003 | Falls |
| 6,520,961 B1 | 2/2003 | Marsh |
| 2002/0147455 A1 | 10/2002 | Carson et al. |

FOREIGN PATENT DOCUMENTS

| | | |
|---|---|---|
| GB | 2110094 | 6/1983 |
| WO | WO-02/094112 | 11/2002 |
| WO | WO-03/086213 | 10/2003 |

OTHER PUBLICATIONS

Canadian Patent Office, Office Action dated Oct. 28, 2010, Application No. 03811627.3-2310/1567046, 2 pages.

PCT Patent Office, International Search Report dated Nov. 16, 2004, Application No. PCT/US03/29435, 1 page.

PCT Patent Office, International Search Report dated Nov. 19, 2004, Application No. PCT/US03/36590, 1 page.

SECTION A-A

SECTION B-B

SECTION C-C

Front

Side

Top

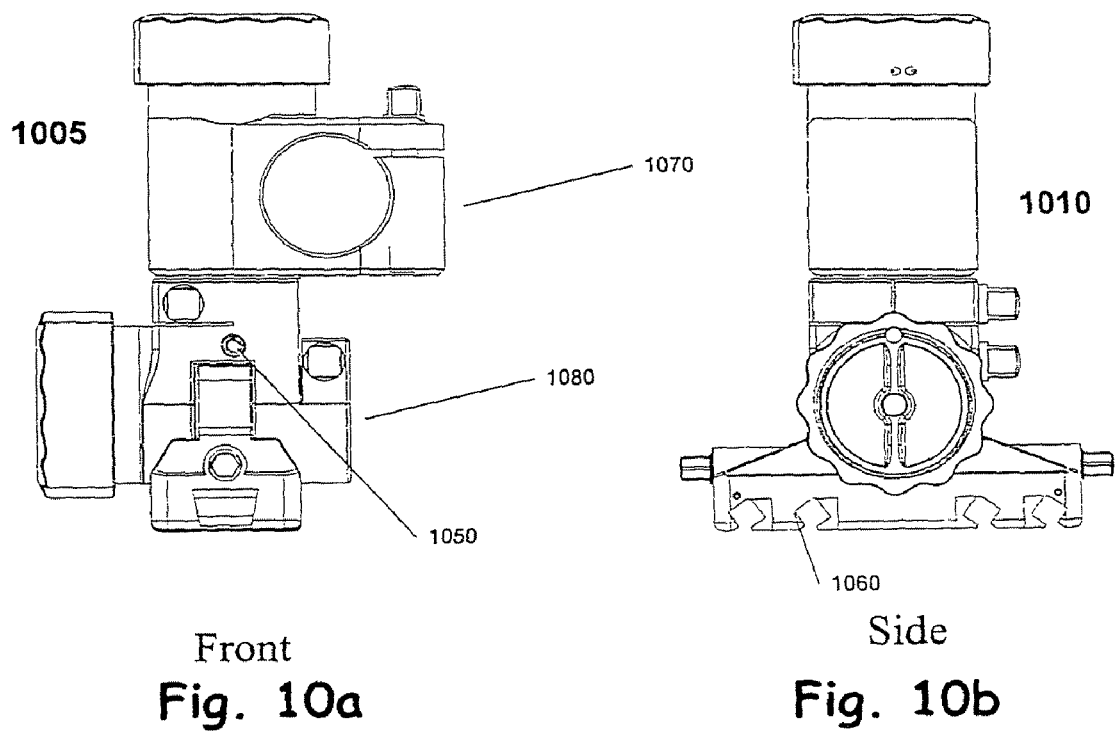
Front
Fig. 10a
Side
Fig. 10b
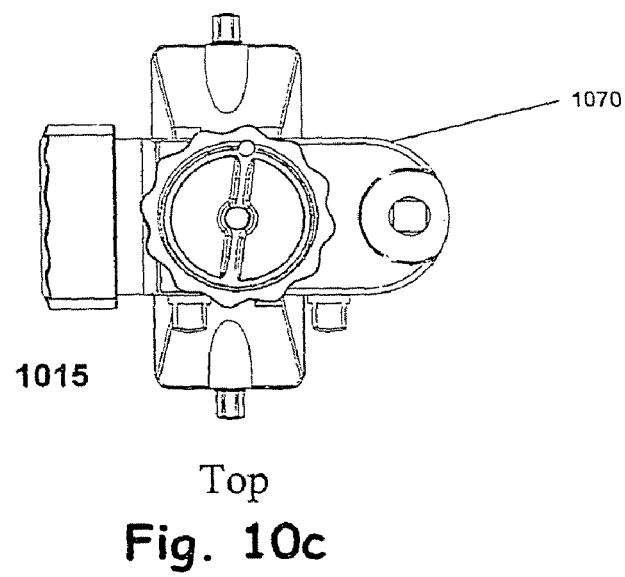
Top
Fig. 10c

Isometric

Front

Side

Top

Isometric

Section A-A

Section B-B

Section C-C

Section D-D

Front

Side

Top

Isometric

Section A-A

1510

Front

1520

Side

1530

Top

1540

Isometric

Section A-A

Front

Side

1630

Top

Isometric

1710

Front

1720

Side

1730

Bottom

1740

Isometric

Section A-A

1810 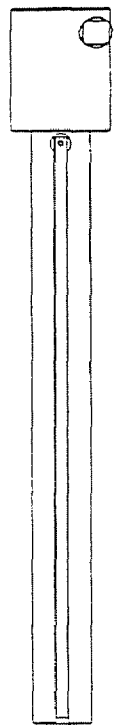
1820 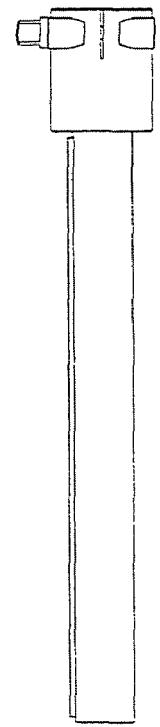
Front
Fig. 18a
Side
Fig. 18b
1830 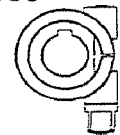
Top
Fig. 18c Front Side Top Isometric

1950

Section A-A

UNILATERAL FIXATOR

CROSS-REFERENCE TO RELATED APPLICATIONS

This application is a continuation of U.S. patent application Ser. No. 10/644,769 filed on Sep. 17, 2003, which claims priority from U.S. Provisional Patent Application No. 60/411,291 filed Sep. 17, 2002, and U.S. Provisional Patent Application No. 60/426,439, filed Nov. 14, 2002. The disclosures of the above applications are incorporated herein by reference.

INTRODUCTION

In orthopedic medicine, physicians often need to correct certain skeletal injuries or deformities with external fixator devices. These deformities can either be an acute or chronic condition that may be corrected over a short or long period of time. These devices use pins or wires attached to the separate bone segments and an external structural frame to align, or fix, the bone segments in a way to aid in repairing the injury or correcting the deformity. When the device is engaged with a patient, the device applies forces to maintain the bone fragments in a configuration prescribed by a physician. Often the physician must gradually adjust the orientation of the bone segments over time, optimally with the capability to adjust the orientation along six degrees of freedom to ensure the bone segments are placed in the correct anatomic condition.

Devices and methods for treating musculoskeletal deformities are well known in the art. Although these devices vary considerably in design, they typically fall into two broad categories, circular ring and unilateral devices. The circular ring device category is exemplified by Ilizarov-type systems, which have two rings connected by linear struts with a fixed or hinged connection at each end of each strut. A device called a space frame, which has two rings connected by six linear struts having a spherical joint at each end arranged in a hexapod configuration, e.g., a Stewart frame, represents an advancement on the original Ilizarov concept. Other embodiments can be combinations of rings being attached to what would be considered a unilater device. These constructs are typically referred to as hybrid devices.

The Ilizarov device is constructed based on the deformity that needs correcting, that is, for a specific patient and a specific deformity on that patient, hinges and struts are added to address each degree of deformity in a specific case. Ilizarov-type devices are often referred to as serial manipulators in that each adjustment relates to a single degree of deformity. This approach requires the frame to be constructed based on the deformity present, resulting in a fairly straightforward method of use but a potentially complex set of multiple and potentially endless configurations. The space frame is a device that conceptually comes in one configuration even though rings and struts can be of differing sizes. The Stewart frame-type space frame is often referred to as a parallel manipulator in that any given adjustment to any of the six struts will result in a change to all six degrees of freedom. This characteristic makes the Stewart frame type device less intuitive to use. A computer program is often required to direct the user in making the adjustments to correct the deformity.

The unilateral device category has several devices that basically consist of a series of orthogonal planar hinges or spherical joints and, in some cases, sliders that can be locked into a particular orientation. Typically these devices can be used to fix bone segments in a particular orientation but not to gradually, and precisely, drive the orientation, since the joints of the device do not have a direct adjustment device associated with each hinge or slider. Instead, the joints of the device must be loosened and then grossly manipulated on the device as a whole. Like the Ilizarov-type circular ring fixators, some of these devices have the ability to drive certain degrees of freedom, typically compression or distraction and, at times, a single revolution about an axis, although these devices often need to be constructed or mounted in a particular orientation depending on the characterization of the deformity. This requirement complicates their use and also necessitates multiple configurations to address the range of deformities that physicians typically encounter. The devices in the prior art do not allow for precise adjustment in six degrees of freedom while the device is engaged with the patient.

Six-degrees-of-freedom refers to movement relative to three orthogonally-opposed axis plus rotation about each of those three axes. These six degrees of freedom are typically referred to as longitudinal, vertical, lateral, pitch, roll, and yaw.

Also, a space frame or unilateral fixator can be grossly manipulated to position the bone fragments of a deformity in the proper place at the beginning of a deformity correction process. However, a physician may need to reposition the fixator throughout the deformity correction process, to effectuate a proper correction of the deformity. Typical space frames and unilateral fixators must be disengaged from the patient, that is, the devices need to be loosened while attached to the patient, and grossly adjusted each time the physician needs to adjust the orientation of the fixator during the deformity correction process. One reason for this limitation of existing devices is that the adjustment mechanisms of the devices do not provide sufficient mechanical advantage or range of motion to accomplish the fine adjustment. This inability to finely adjust the fixator in place reduces the utility of these fixators.

The present teachings provide a unilateral fixator and more specifically to a unilateral fixator that addresses a variety of six-degrees-of-freedom musculoskeletal deformity through both gross and fine manipulation of the fixator during the deformity correction process.

SUMMARY

The present teachings provide a unilateral external fixator device that allows for gross manipulation and fine adjustment of deformities in six degrees of freedom. The present teachings may require only one configuration of the fixator to address a wide range of deformities. The present teachings may include an adjustment mechanism that offers superior mechanical advantage. This system provides a unilateral device with six degrees of freedom that can correct, through both gross and find adjustments, bone deformities in any direction without the need to continually disengage the fixator from the patent during a deformity correction process.

In one aspect, the present teachings provide a unilateral fixator having a strut assembly and two compound movable joints. Each compound movable joint comprises two revolute joints. One of the compound movable joints is capable of rotating about the linear axis of the strut assembly and the other compound movable joint is capable of moving along the linear axis of the strut assembly. The fixator also comprises a bone fragment attachment apparatus attached to each of the compound movable joints.

In another aspect, one of the compound movable joints is fixed relative to the strut and comprises three revolute joints and the other compound movable joint comprises two revolute joints and is capable of moving along the linear axis of the strut assembly. The fixator also comprises a bone fragment attachment apparatus attached to each of the first and second compound movable joints.

In another aspect of the present teachings, a compound movable joint for a unilateral fixator comprises a left-hand helical spline, a right-hand helical spline, and a thrust washer positioned between the right-hand helical spline and the left-hand helical spline. The compound movable joint also comprises a helical spool that may slide within the right-hand helical spline and the left hand helical spline and may be rotationally engaged to the right-hand helical spline and the left hand helical spline. The compound movable joint also has a cap screw axially clamping together the left-hand helical spline, the right-hand helical spline, and the thrust washer and allowing for a fine adjustment of the reduction mechanism while the bone fragment attachment apparatus is engaged with a bone fragment.

More generally, the present teachings provide a device that can address a six-degrees-of-freedom musculoskeletal deformity, that is, a deformity having anterior-posterior (AP), lateral, and axial offsets and angulations or any subset thereof. The device can placed on the deformity in any particular orientation within the limits of practicality and can reduce the deformity to the anatomic state without requiring multiple configurations of the device. Additionally, the device can allow for the gross manipulation of the deformity for acute cases and then allow for additional precise, fine adjustment to be administered during a deformity correction process while the device remains engaged with the patient to fully restore the deformity to the correct anatomic condition through an adjustment mechanism that offers a high degree of mechanical advantage.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 provides an image of a unilateral fixator in accordance with an exemplary embodiment of the present teachings.

Figure 2:
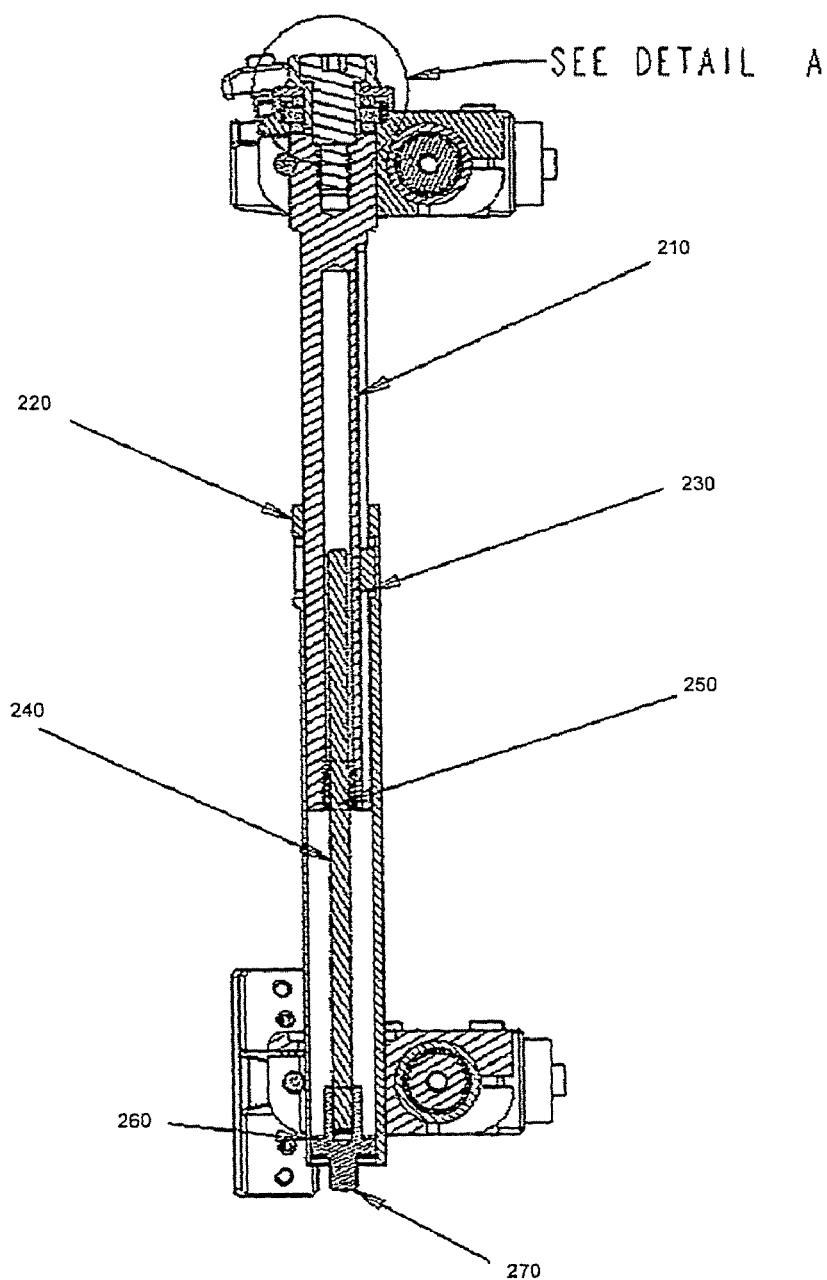

FIG. 2 provides an image of Section A-A of the unilateral fixator provided in FIG. 1.

Figure 3:
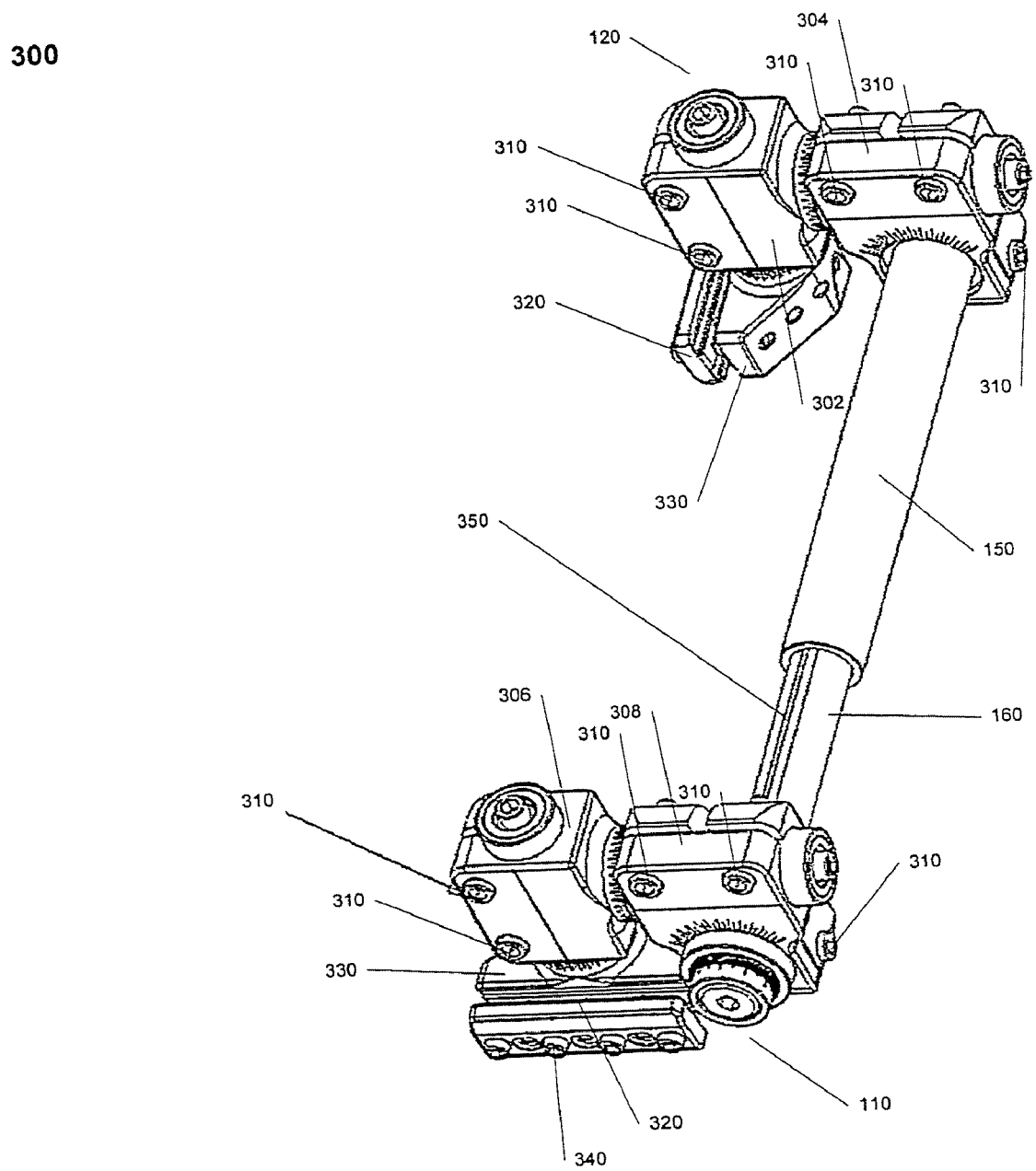

FIG. 3 provides an isomeric image of the exemplary unilateral fixator provided in FIG. 1.

Figure 4B:
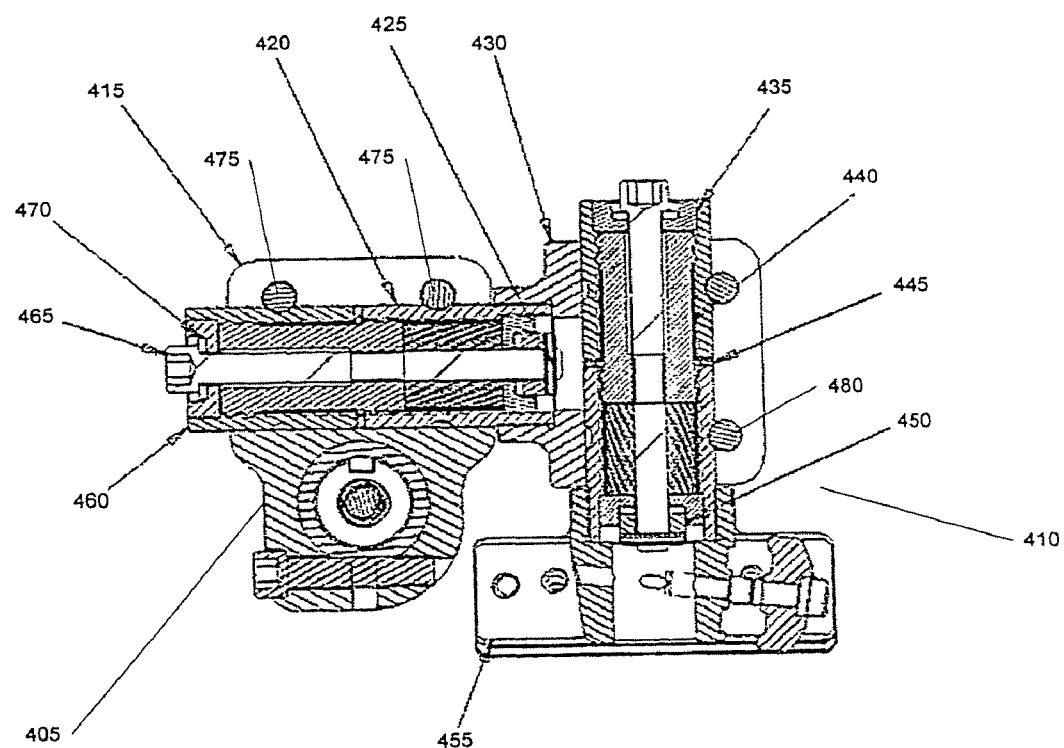
Figure 4A:
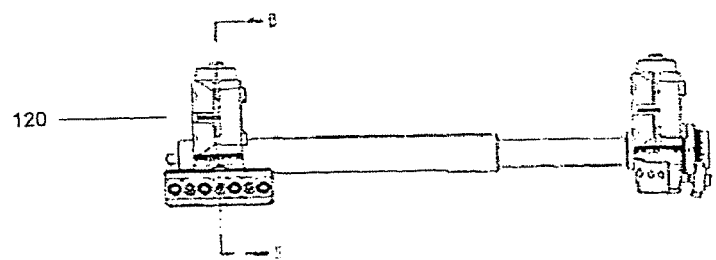

FIG. 4a provides an alternative image of an exemplary unilateral fixator.

FIG. 4b provides an image of Section B-B of the unilateral fixator provided in FIG. 4a.

Figure 5:
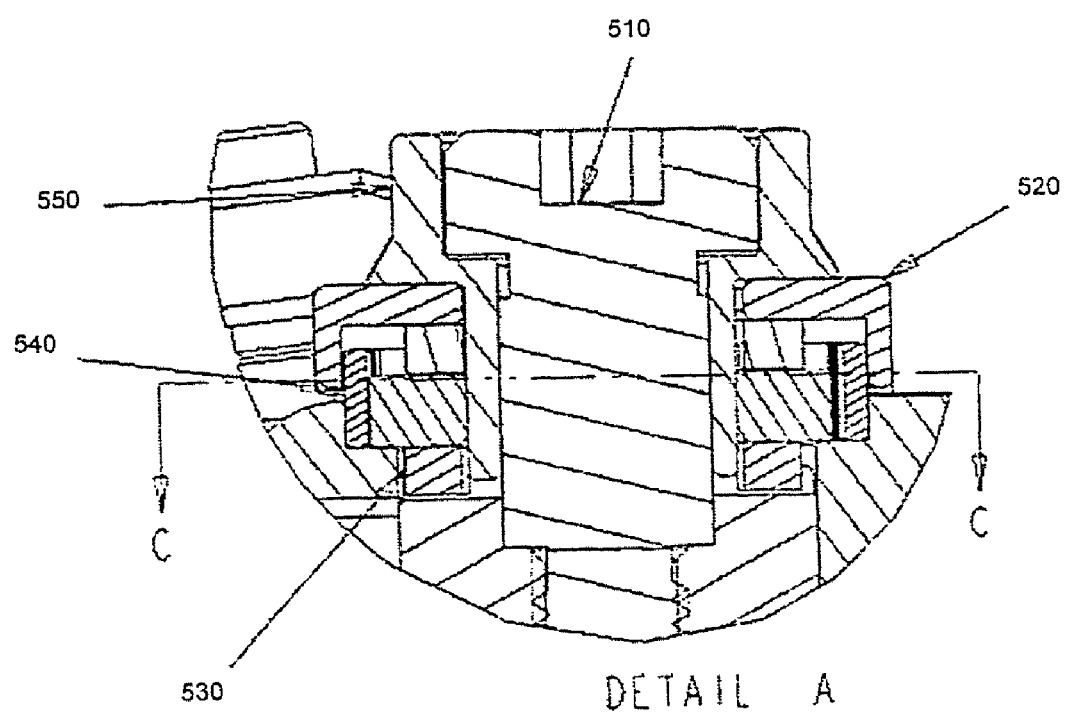

FIG. 5 provides an image of Detail A of the unilateral fixator provided in FIG. 2.

Figure 6:
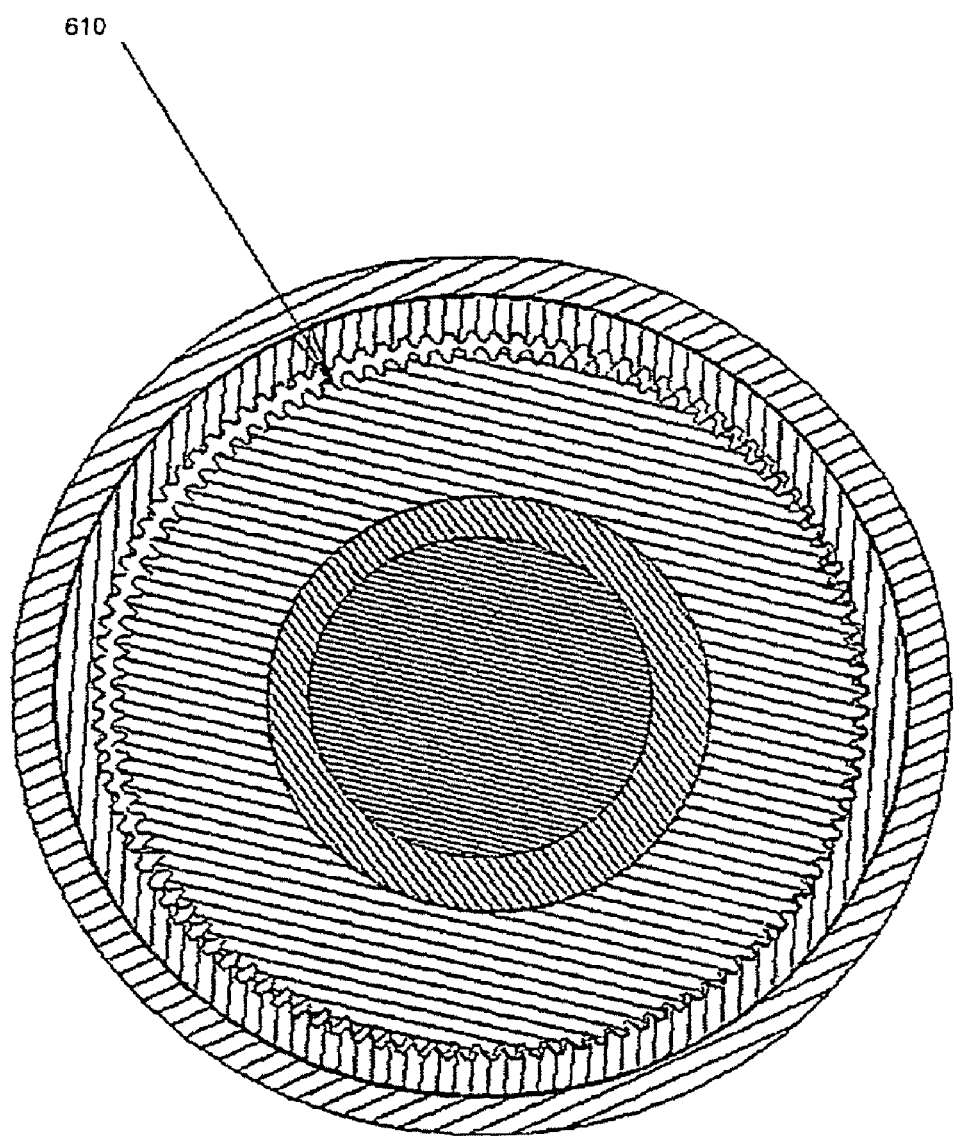

FIG. 6 provides an image of Section C-C of Detail A of FIG. 3 showing a gear assembly for a unilateral fixator in accordance with an exemplary embodiment of the present teachings.

Figure 7:
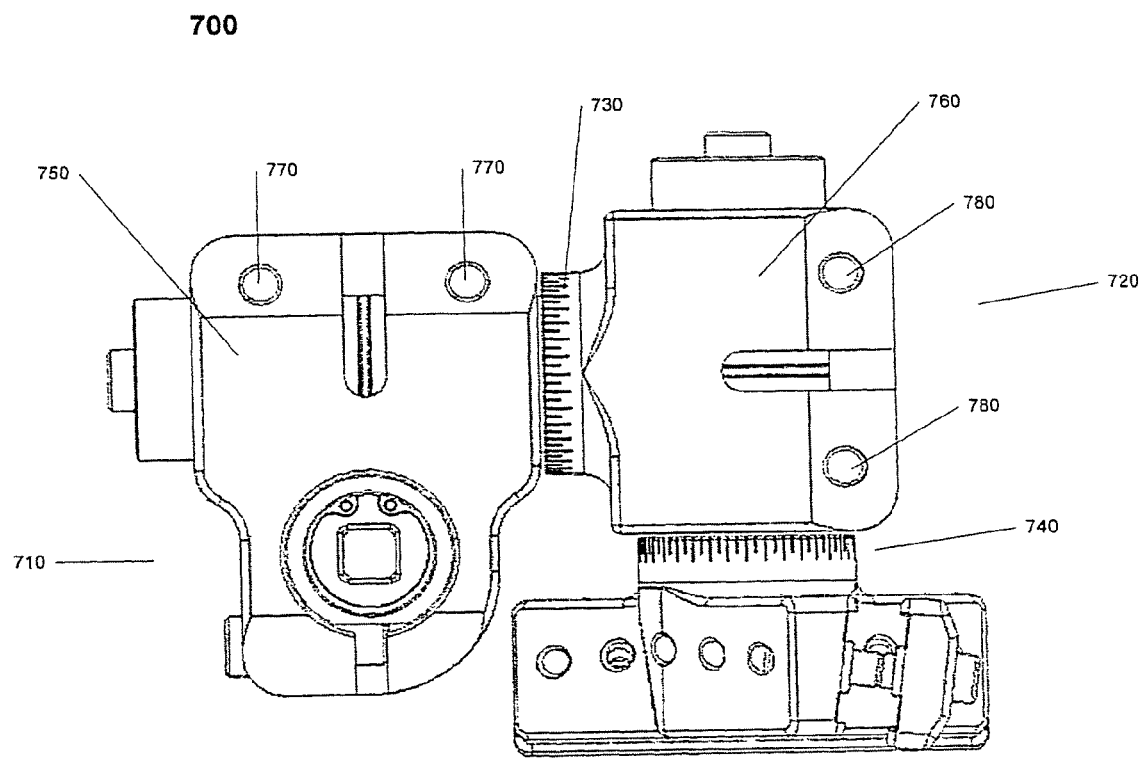

FIG. 7 provides an image of a compound movable joint in accordance with an exemplary embodiment of the present teachings.

Figures 8A, 8B, 8C:
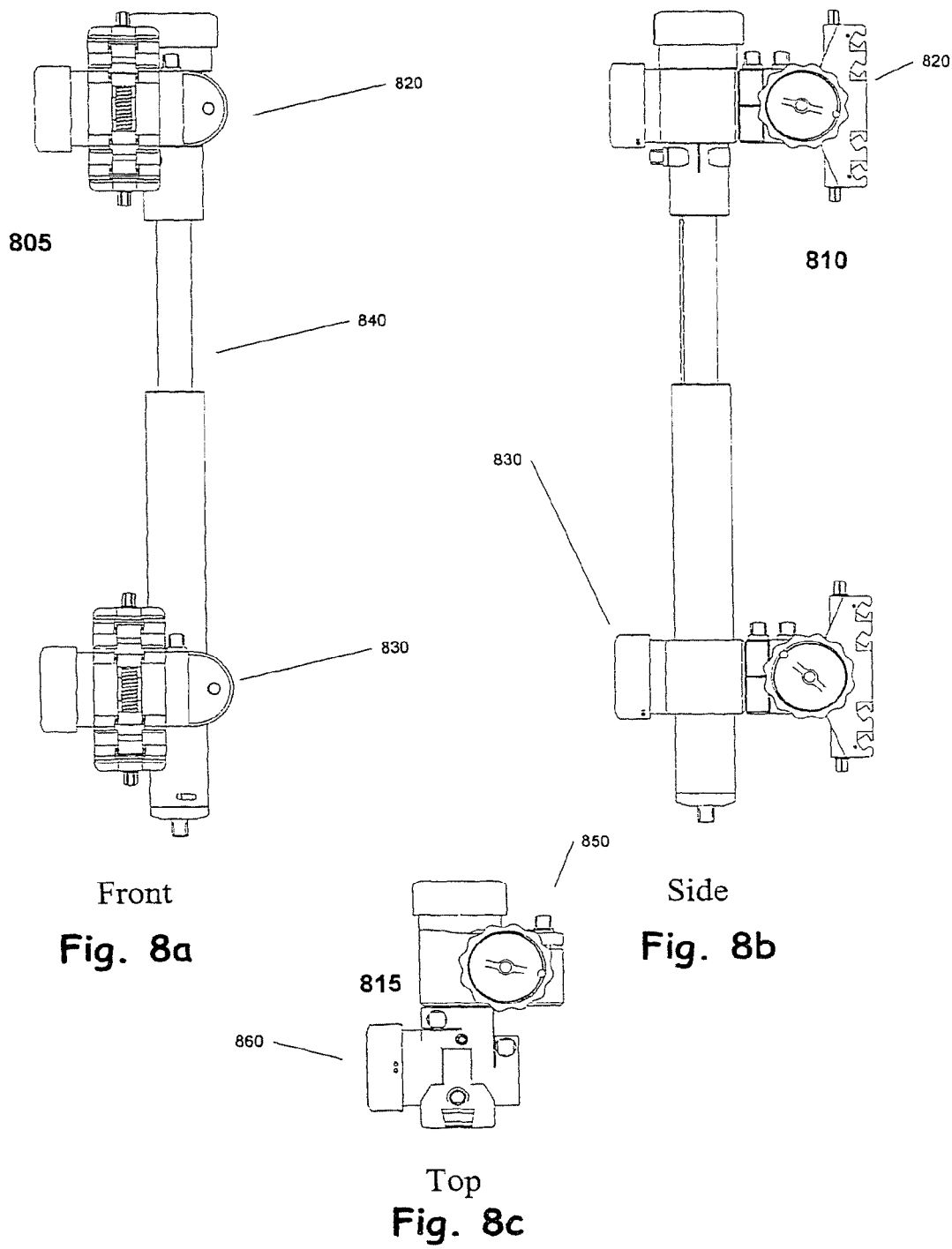

FIG. 8a provides a front image of a unilateral fixator in accordance with an alternative exemplary embodiment of the present teachings.

FIG. 8b provides a side image of a unilateral fixator in accordance with an alternative exemplary embodiment of the present teachings.

FIG. 8c provides a top image of a unilateral fixator in accordance with an alternative exemplary embodiment of the present teachings.

Figure 9:
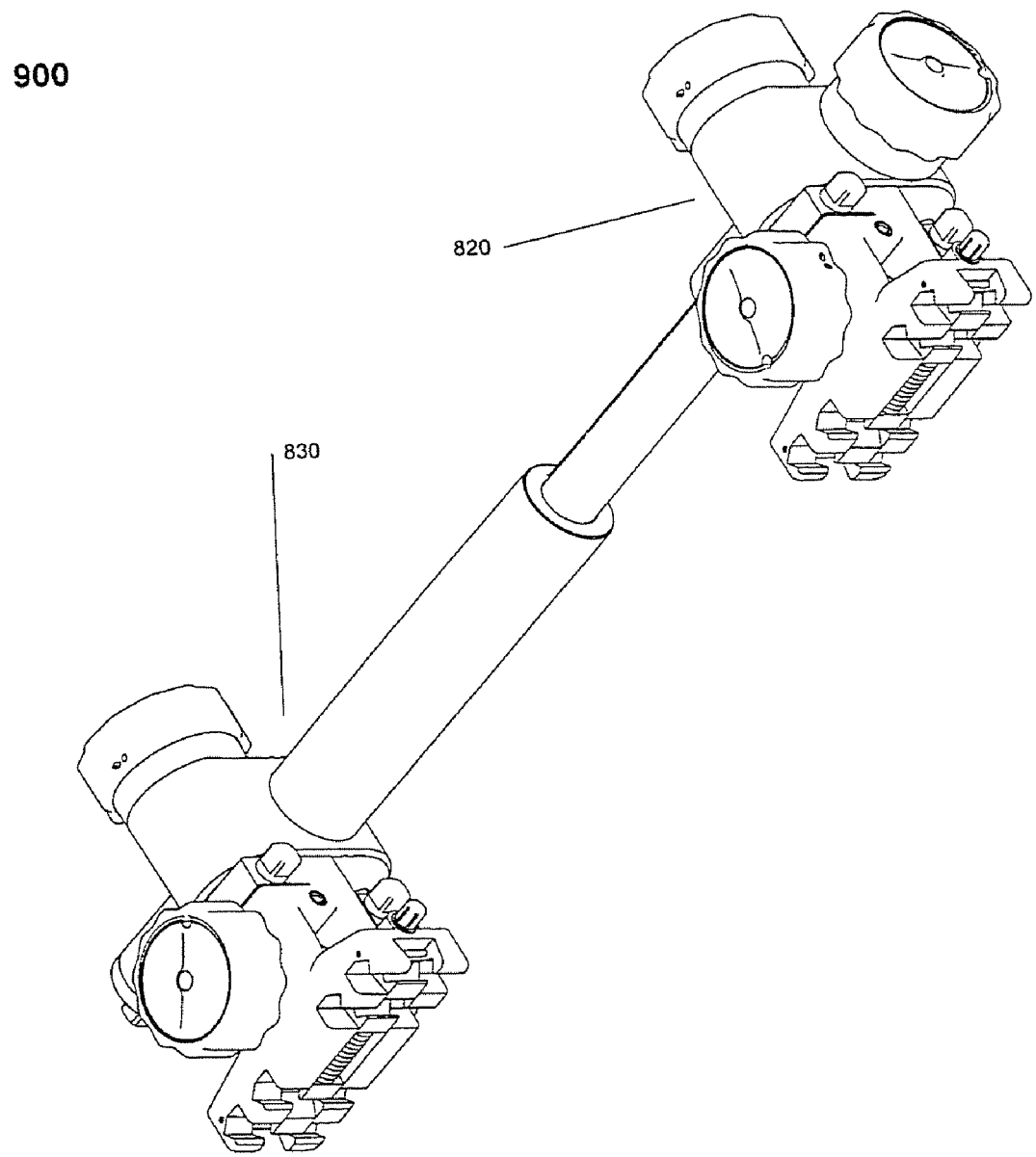

FIG. 9 provides an isomeric image of a unilateral fixator in accordance with an alternative exemplary embodiment of the present teachings.

FIG. 10a provides a front image of a compound movable joint in accordance with an alternative exemplary embodiment of the present teachings.

FIG. 10b provides a side image of a compound movable joint in accordance with an alternative exemplary embodiment of the present teachings.

FIG. 10c provides a top image of a compound movable joint in accordance with an alternative exemplary embodiment of the present teachings.

Figure 11:
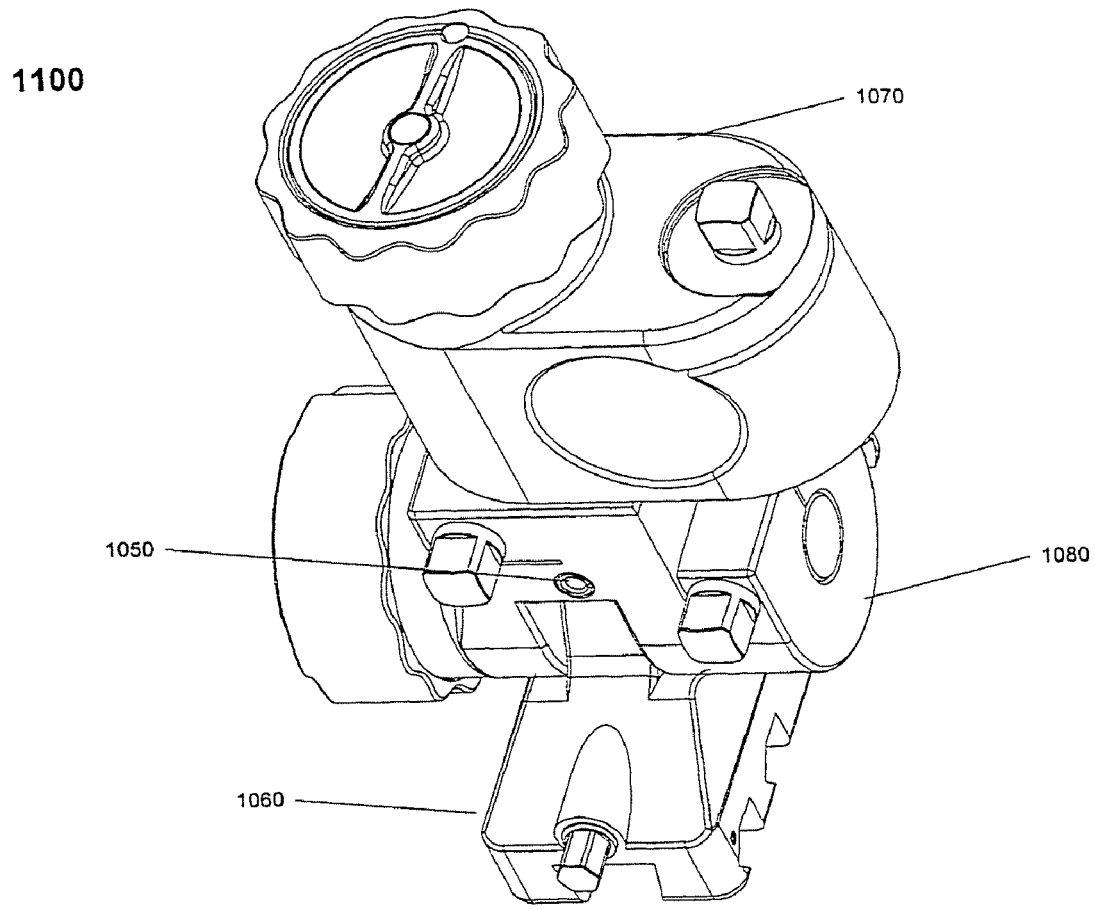

FIG. 11 provides an isomeric image of a compound movable joint in accordance with an alternative exemplary embodiment of the present teachings.

Figure 12A:
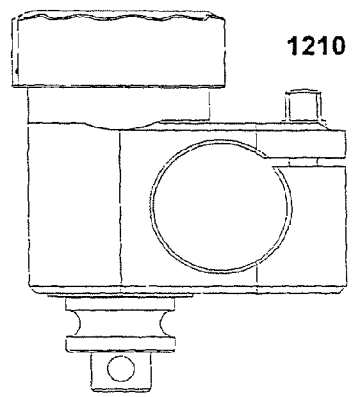

FIG. 12a provides a front image of the first of two revolute joints of a compound movable joint in accordance with an alternative exemplary embodiment of the present teachings.

Figure 12B:
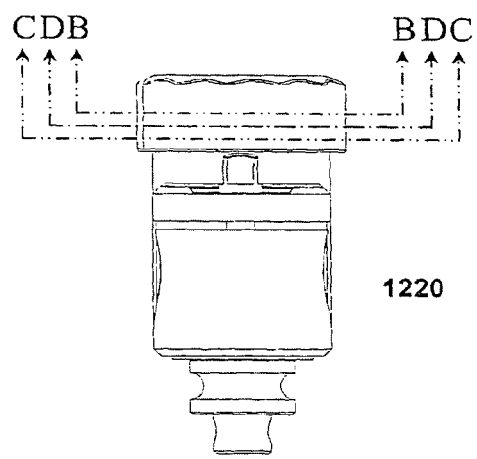

FIG. 12b provides a side image of the first of two revolute joints of a compound movable joint in accordance with an alternative exemplary embodiment of the present teachings.

Figure 12C:
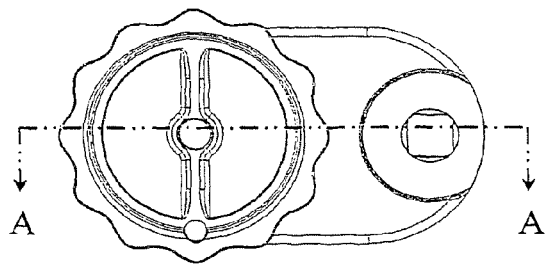

FIG. 12c provides a top image of the first of two revolute joints of a compound movable joint in accordance with an alternative exemplary embodiment of the present teachings.

Figure 12D:
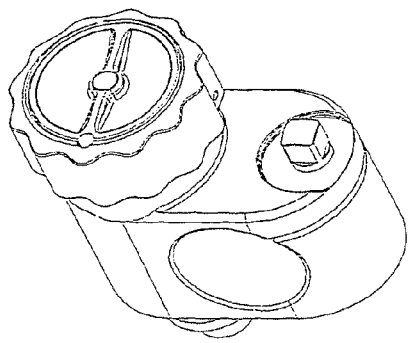

FIG. 12d provides an isomeric image of the first of two revolute joints of a compound movable joint in accordance with an alternative exemplary embodiment of the present teachings.

Figure 12E:
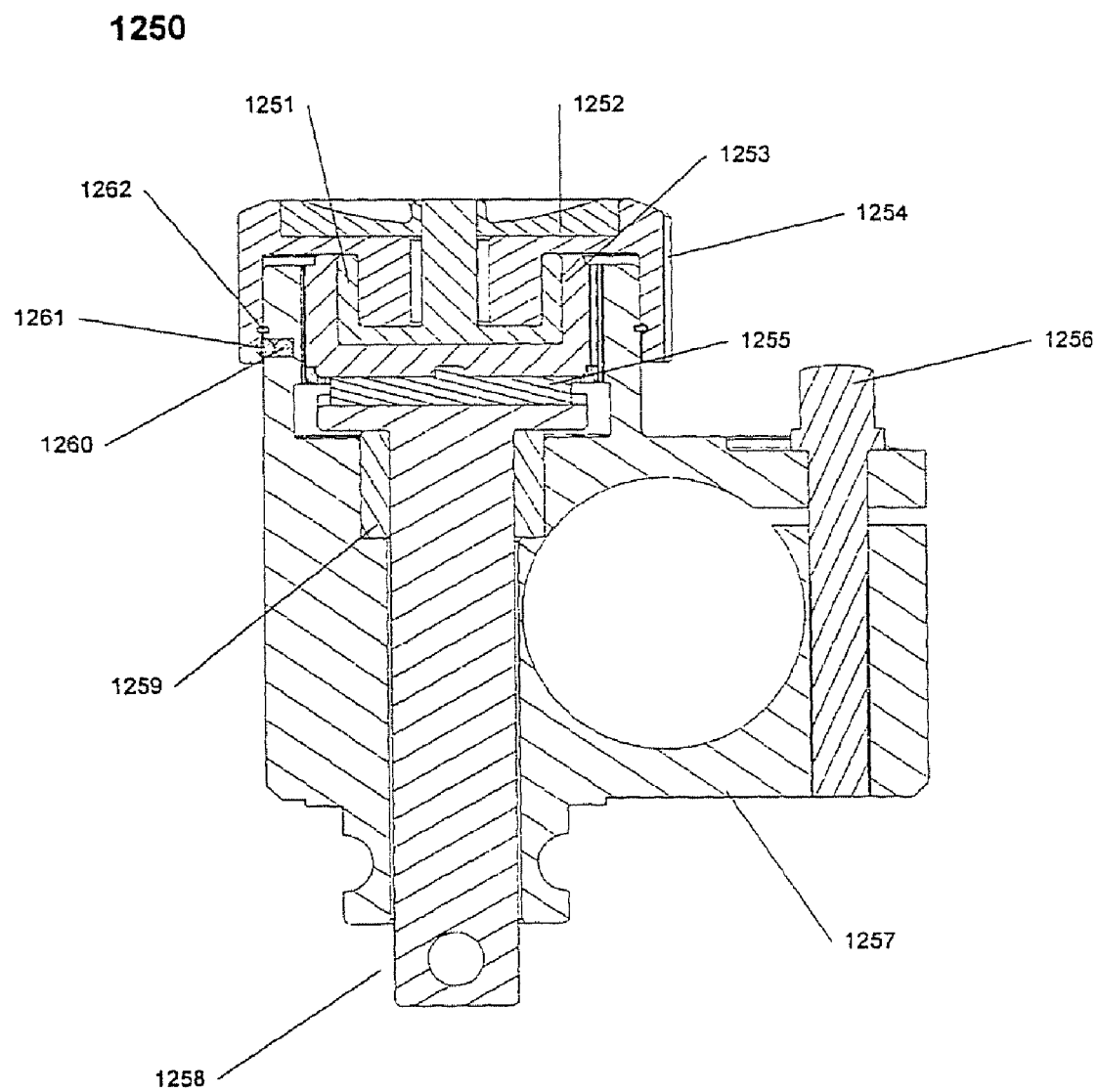

FIG. 12e provides an image of Section A-A of the first of two revolute joints of the compound movable joint provided in FIG. 12c.

Figure 12F:
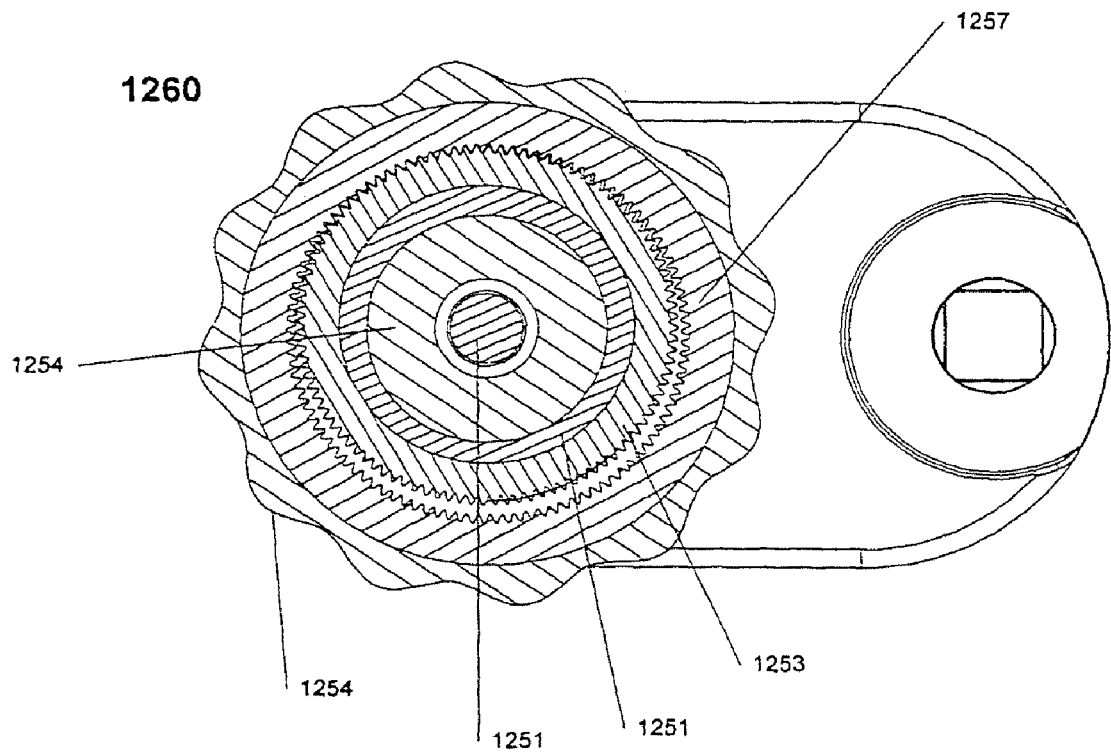

FIG. 12f provides an image of Section B-B of the first of two revolute joints of the compound movable joint provided in FIG. 12b.

Figure 12G:
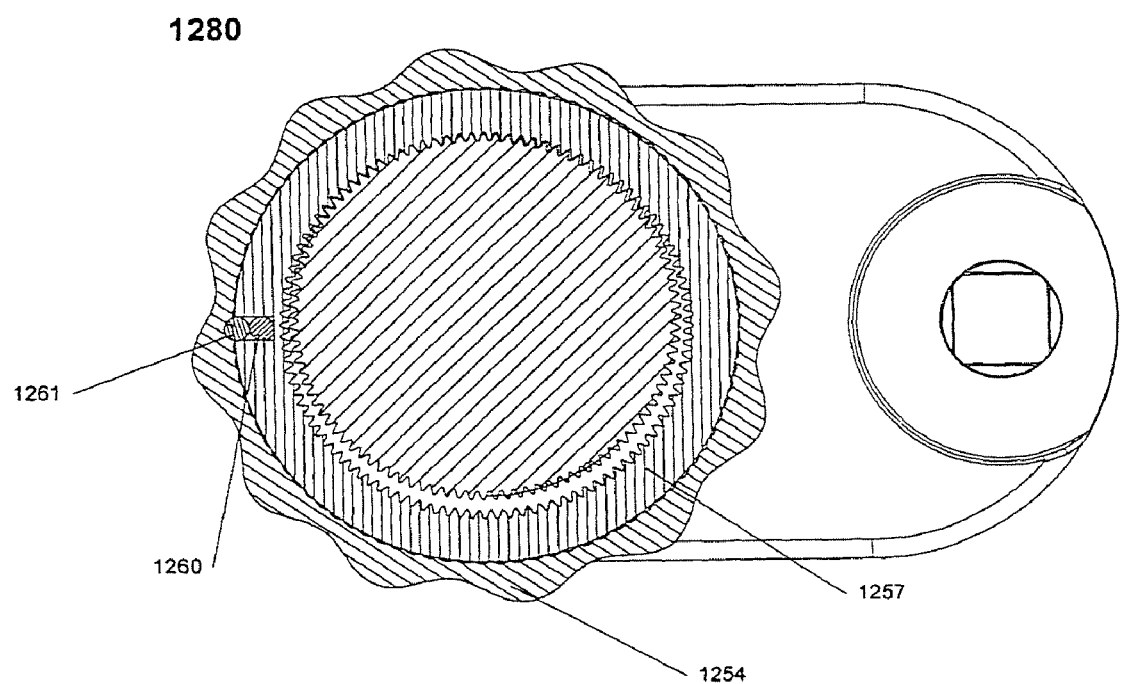

FIG. 12g provides an image of Section C-C of the first of two revolute joints of the compound movable joint provided in FIG. 12b.

Figure 12H:
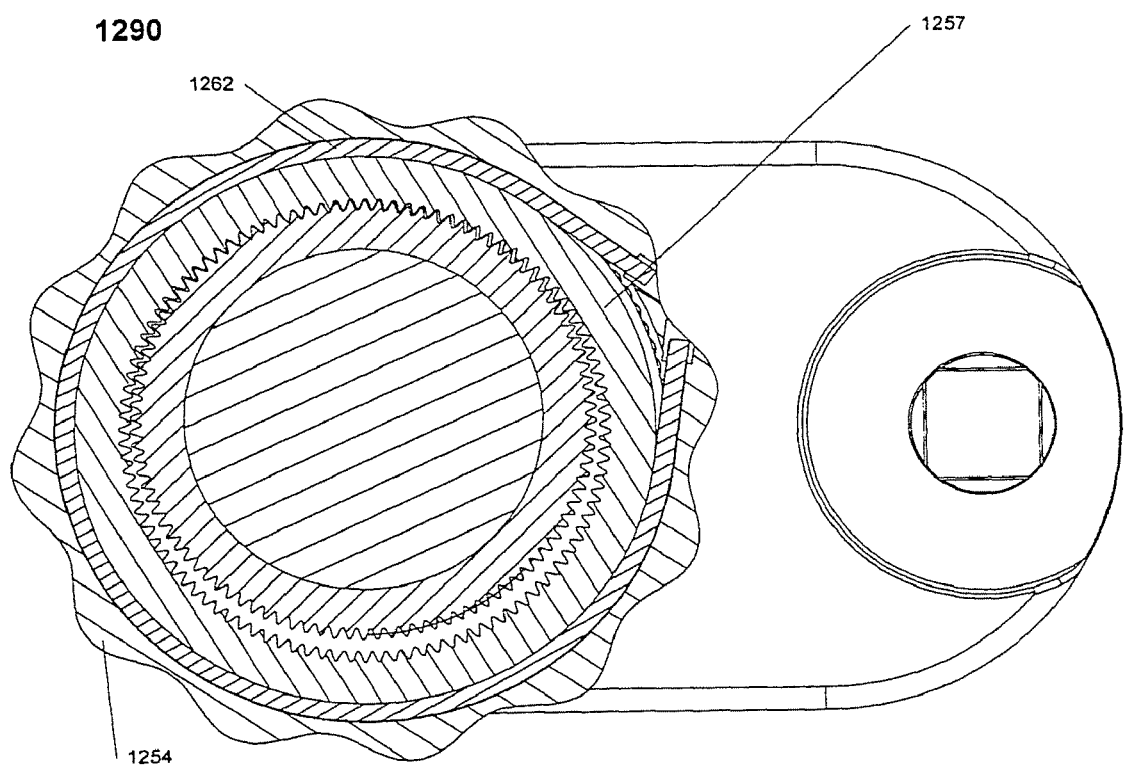

FIG. 12h provides an image of Section D-D of the first of two revolute joints of the compound movable joint provided in FIG. 12b.

Figure 13:
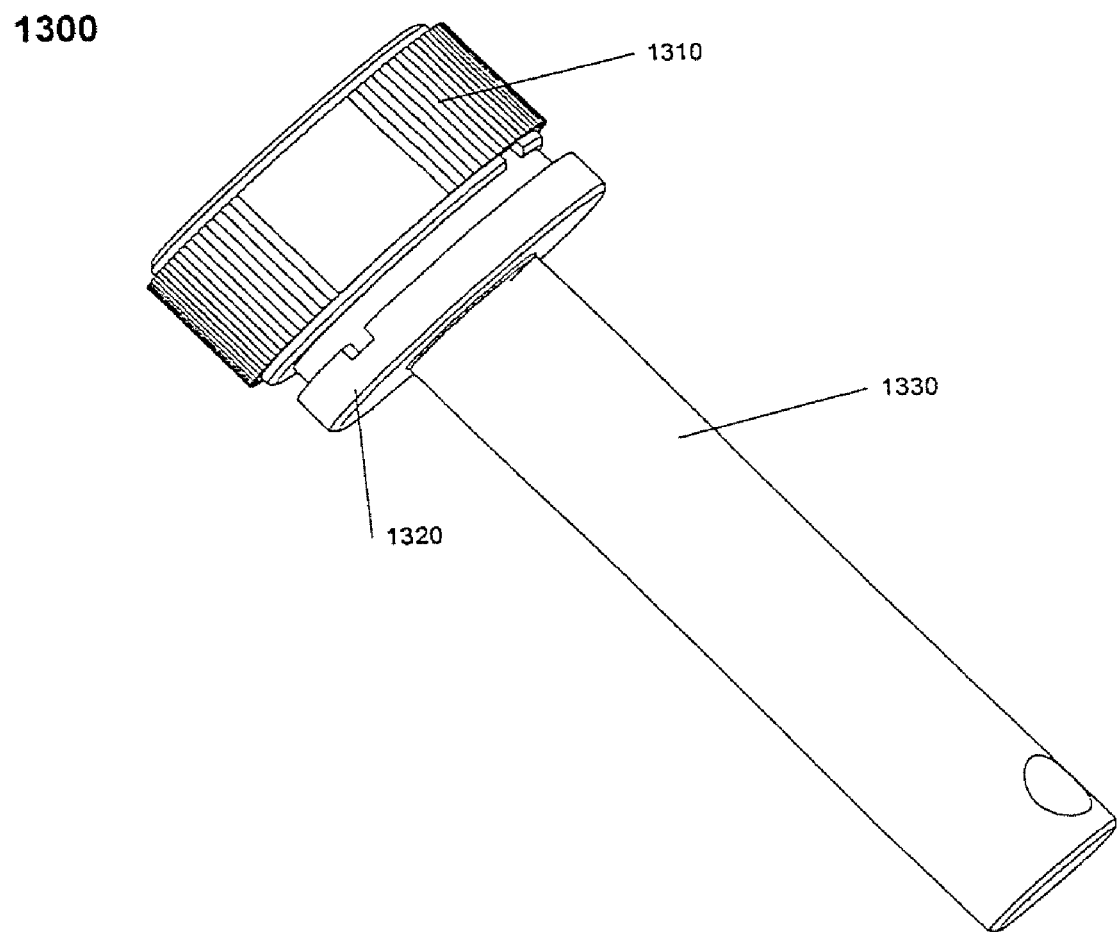

FIG. 13 provides a perspective view of the drive mechanism of the first of two revolute joints of a compound movable joint in accordance with an exemplary embodiment of the present teachings.

Figure 14A:
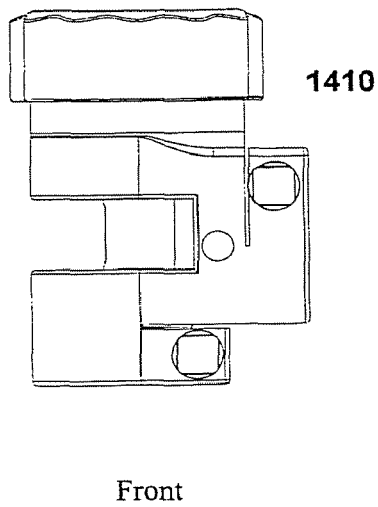

FIG. 14a provides a front image of the second of two revolute joints of a compound movable joint in accordance with an alternative exemplary embodiment of the present teachings.

Figure 14B:
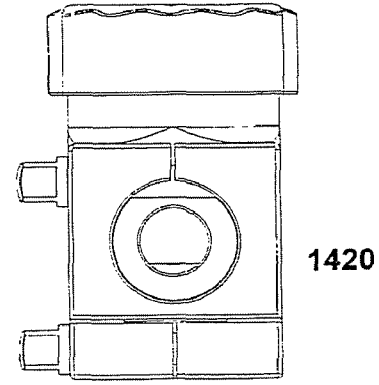

FIG. 14b provides a side image of the second of two revolute joints of a compound movable joint in accordance with an alternative exemplary embodiment of the present teachings.

Figure 14C:
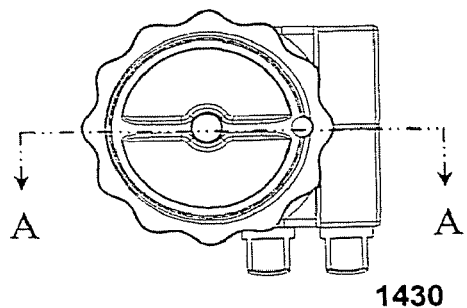

FIG. 14c provides a top image of the second of two revolute joints of a compound movable joint in accordance with an alternative exemplary embodiment of the present teachings.

Figure 14D:
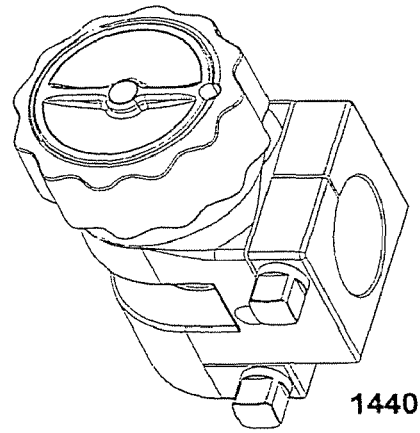

FIG. 14d provides an isomeric image of the second of two revolute joints of a compound movable joint in accordance with an alternative exemplary embodiment of the present teachings.

Figure 14E:
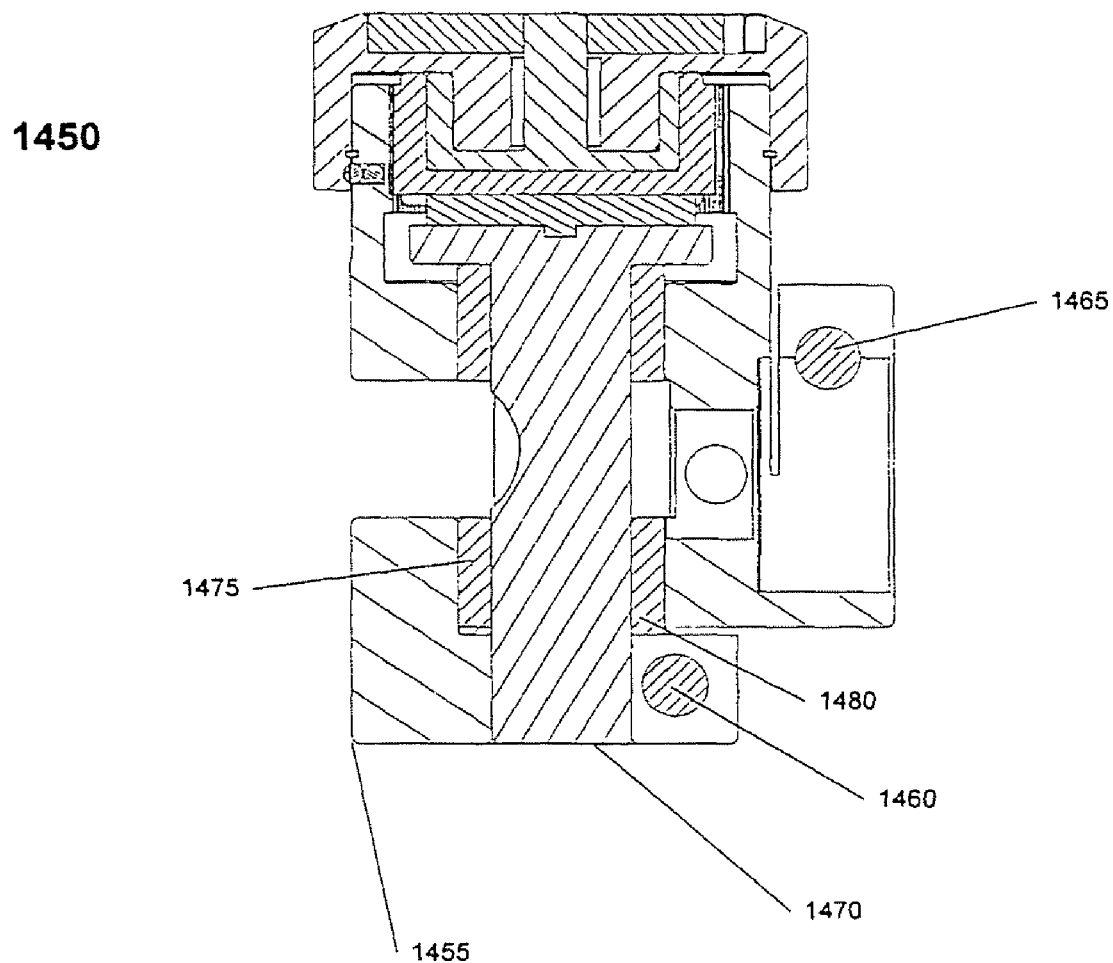

FIG. 14e provides an image of Section A-A of the second of two revolute joints of a compound movable joint provided in FIG. 14c.

Figure 15A:
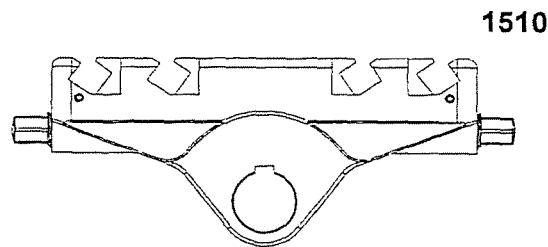

FIG. 15a provides a front image of a pin clap unit in accordance with an exemplary embodiment of the present teachings.

Figure 15B:
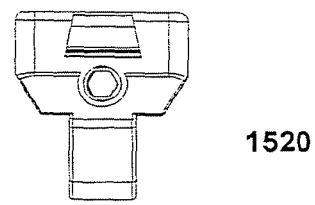

FIG. 15b provides a side image of a pin clap unit in accordance with an exemplary embodiment of the present teachings.

Figure 15C:
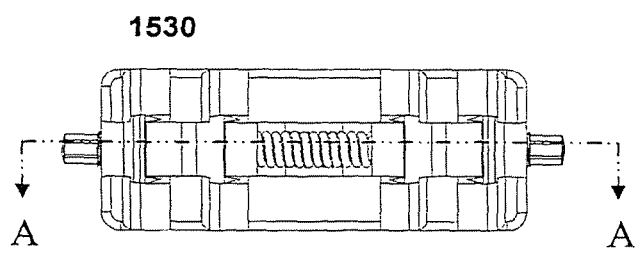

FIG. 15c provides a top image of a pin clap unit in accordance with an exemplary embodiment of the present teachings.

Figure 15D:
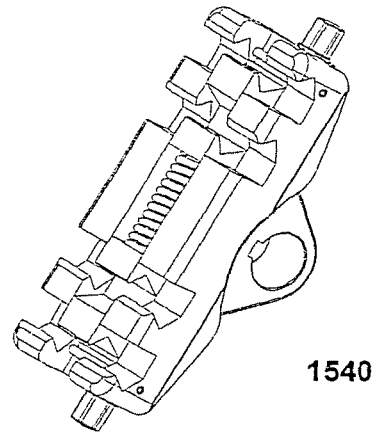

FIG. 15d provides an isomeric image of a pin clap unit in accordance with an exemplary embodiment of the present teachings.

Figure 15E:
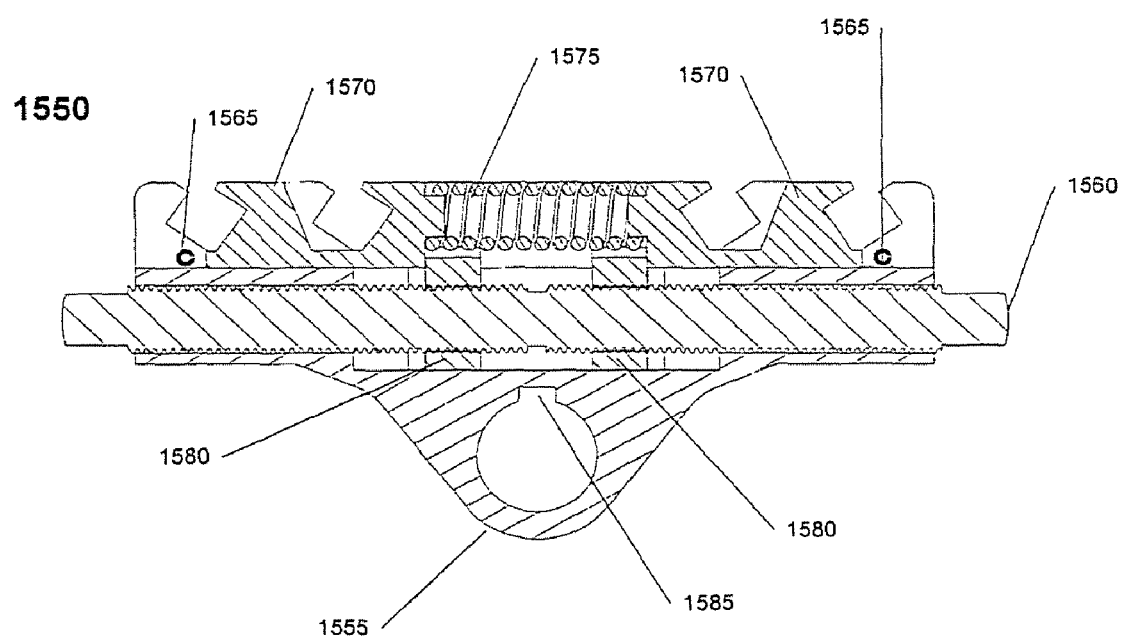

FIG. 15e provides an image of Section A-A of the pin clap unit provided in FIG. 15c.

Figure 16A:
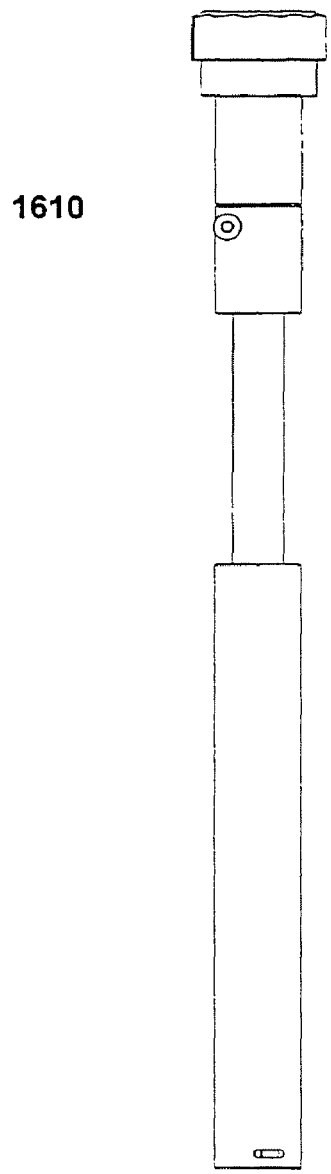

FIG. 16a provides a front image of a strut structure in accordance with an alternative exemplary embodiment of the present teachings.

Figure 16B:
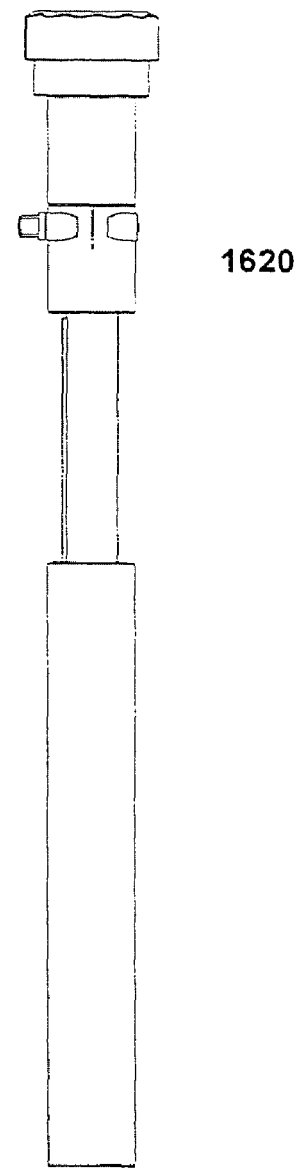

FIG. 16b provides a side image of a strut structure in accordance with an alternative exemplary embodiment of the present teachings.

Figure 16C:
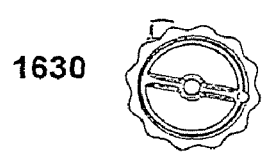

FIG. 16c provides a top image of a strut structure in accordance with an alternative exemplary embodiment of the present teachings.

Figure 16D:
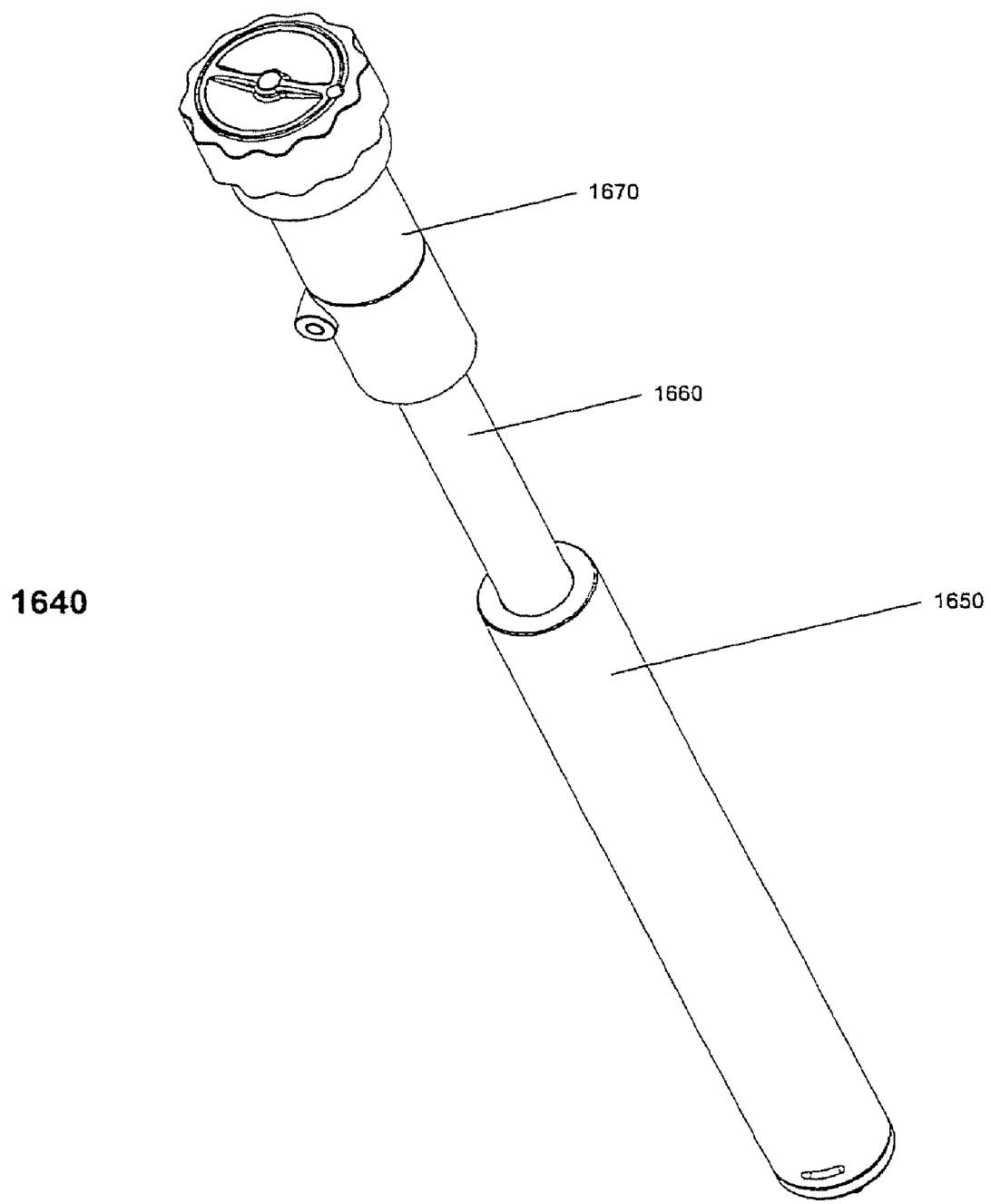

FIG. 16d provides an isomeric image of a strut structure in accordance with an alternative exemplary embodiment of the present teachings.

Figure 17A:
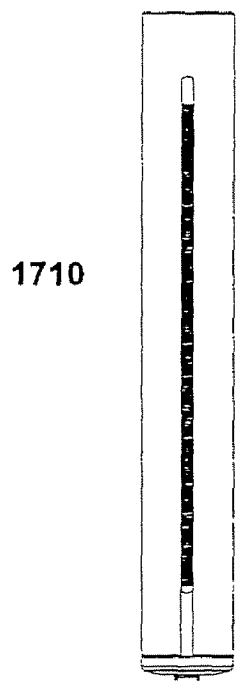

FIG. 17a provides a front image of a base tube assembly in accordance with an alternative exemplary embodiment of the present teachings.

Figure 17B:
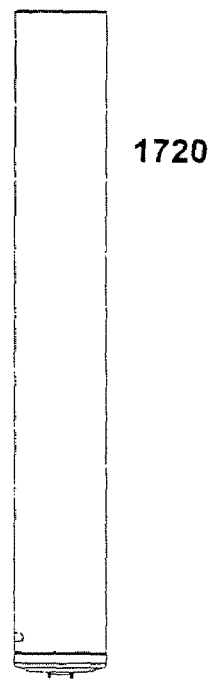

FIG. 17b provides a side image of a base tube assembly in accordance with an alternative exemplary embodiment of the present teachings.

Figure 17C:
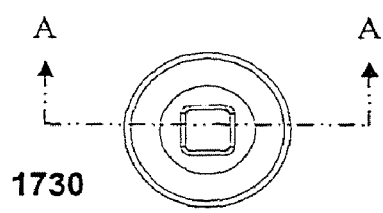

FIG. 17c provides a bottom image of a base tube assembly in accordance with an alternative exemplary embodiment of the present teachings.

Figure 17D:
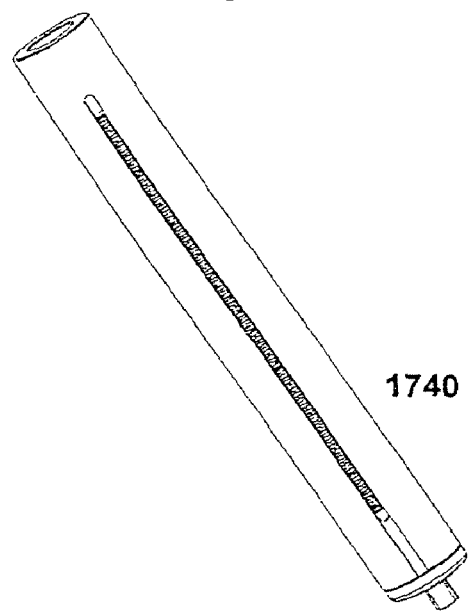

FIG. 17d provides an isomeric image of a base tube assembly in accordance with an alternative exemplary embodiment of the present teachings.

Figure 17E:
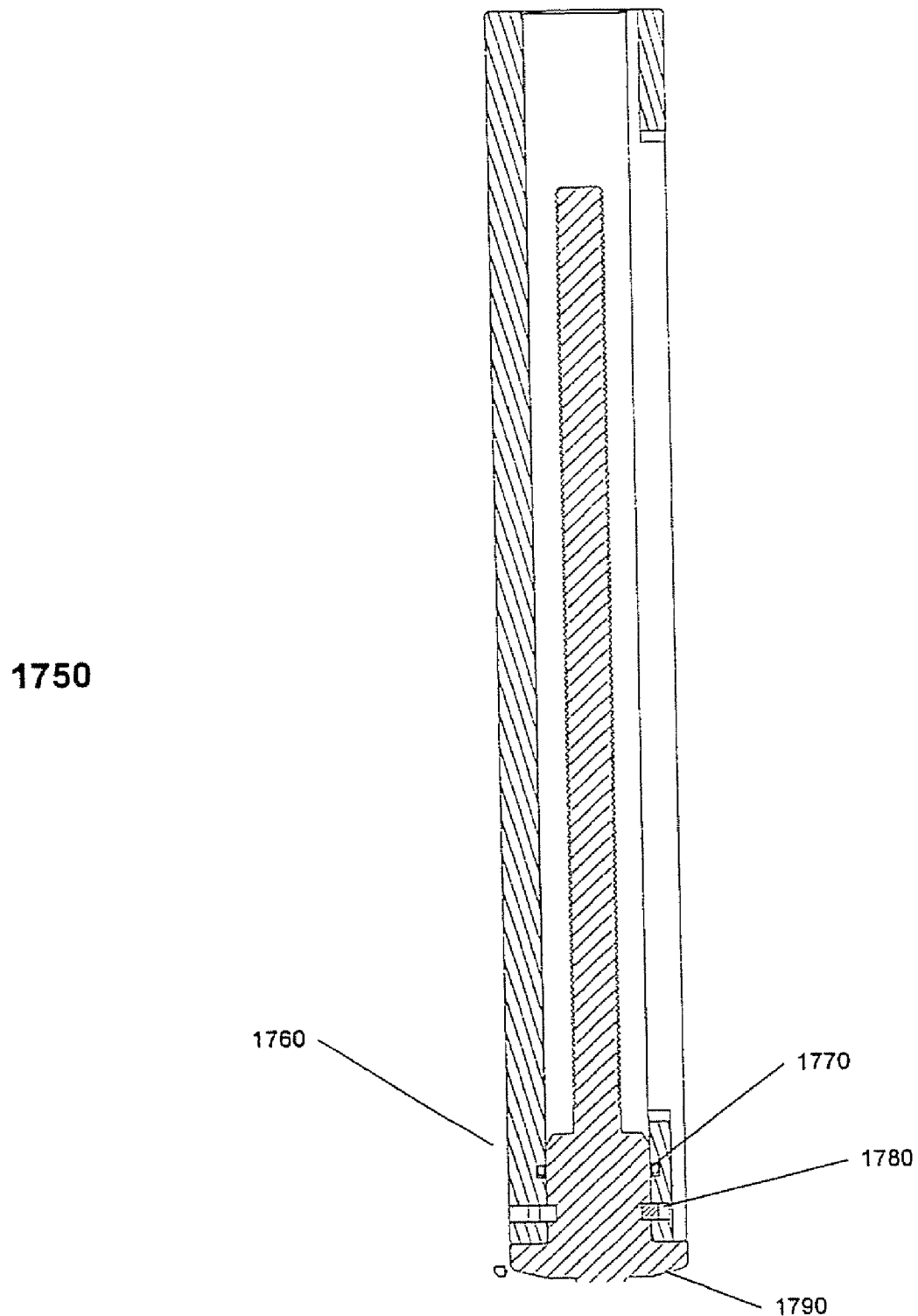

FIG. 17e provides an image of Section A-A of the base tube assembly provided in FIG. 17c.

FIG. 18a provides a front image of a top tube assembly in accordance with an alternative exemplary embodiment of the present teachings.

FIG. 18b provides a side image of a top tube assembly in accordance with an alternative exemplary embodiment of the present teachings.

FIG. 18c provides a top image of a top tube assembly in accordance with an alternative exemplary embodiment of the present teachings.

Figure 18D:
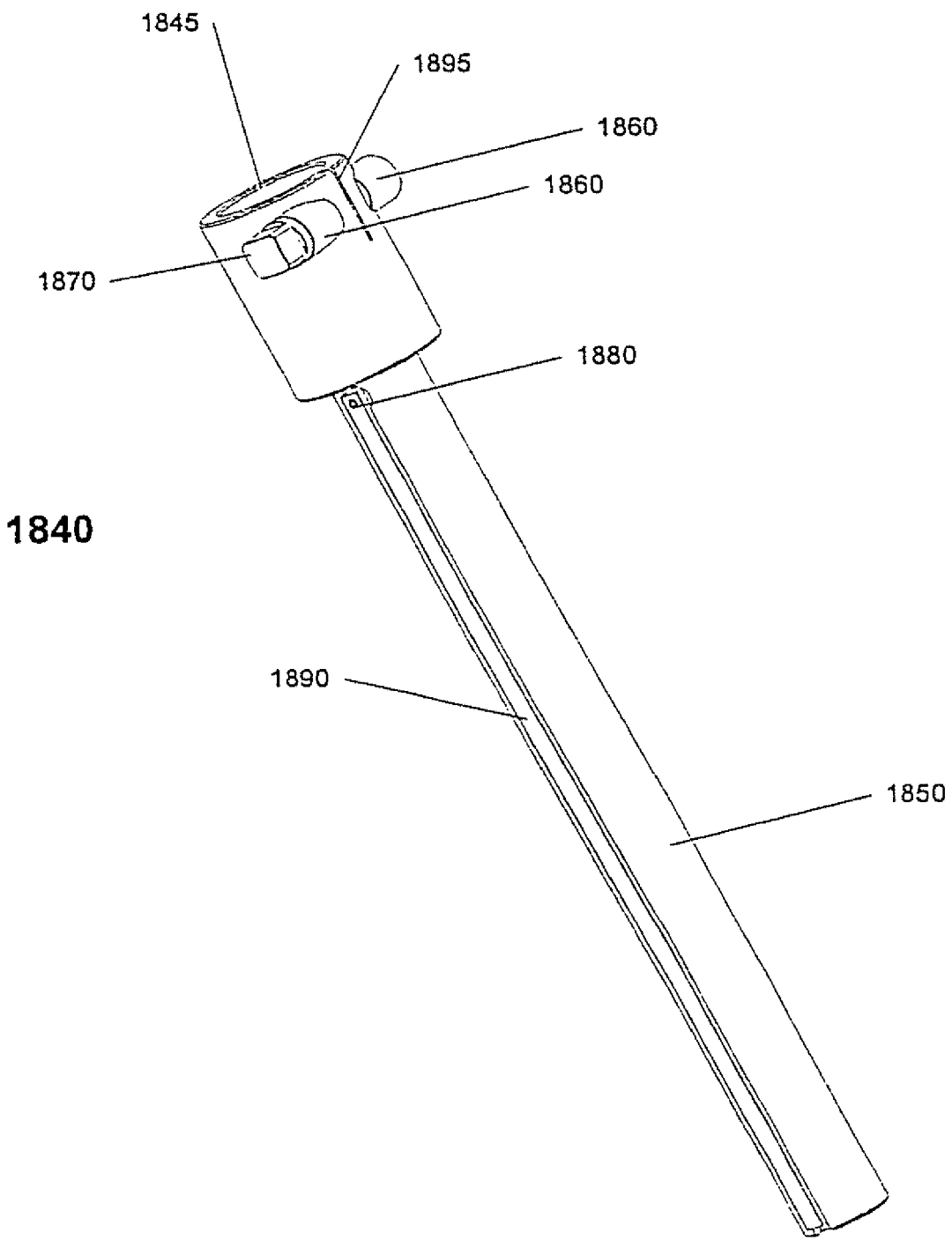

FIG. 18d provides an isomeric image of a top tube assembly in accordance with an alternative exemplary embodiment of the present teachings.

Figure 19A:
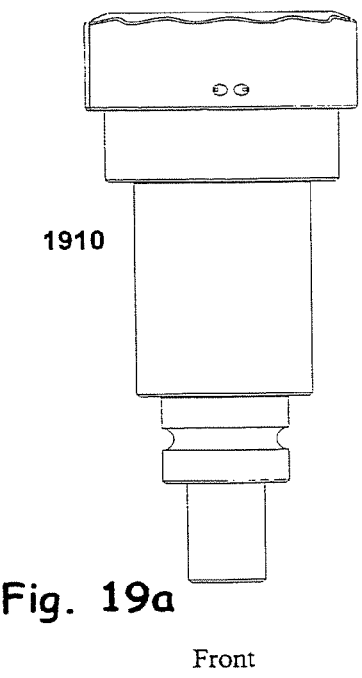

FIG. 19a provides a front image of a yaw joint of the strut structure of FIG. 16 in accordance with an alternative exemplary embodiment of the present teachings.

Figure 19B:
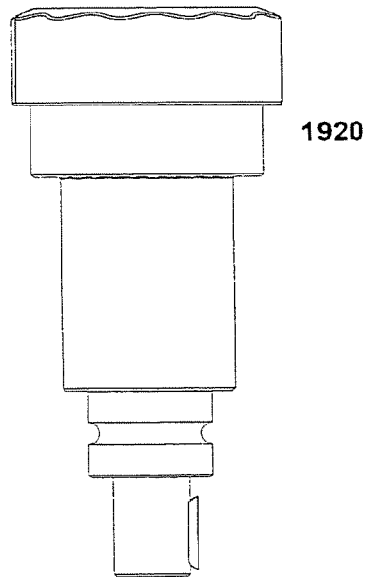

FIG. 19b provides a side image of a yaw joint of the strut structure of FIG. 16 in accordance with an alternative exemplary embodiment of the present teachings.

Figure 19C:
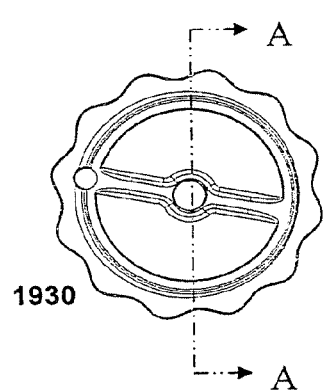

FIG. 19c provides a bottom image of a yaw joint of the strut structure of FIG. 16 in accordance with an alternative exemplary embodiment of the present teachings.

Figure 19D:
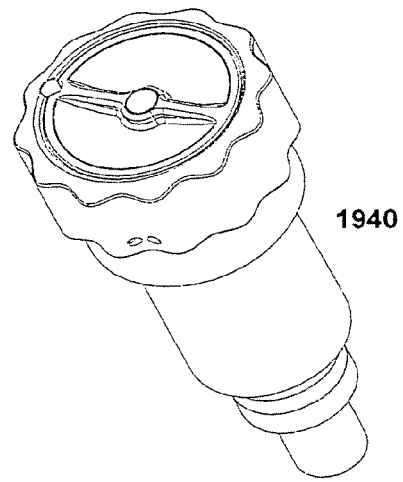

FIG. 19d provides an isomeric image of a yaw joint of the strut structure of FIG. 16 in accordance with an alternative exemplary embodiment of the present teachings.

Figure 19E:
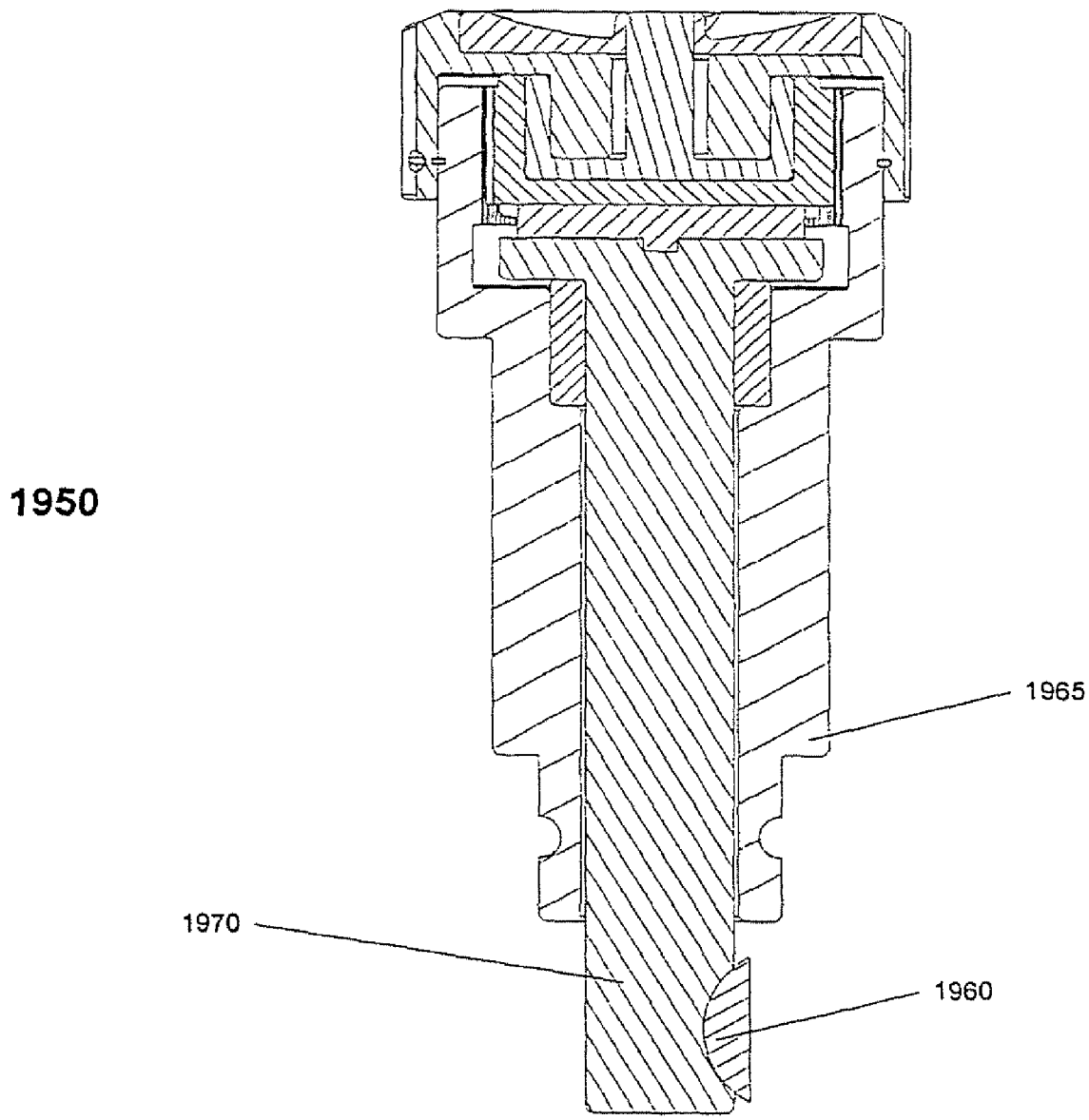

FIG. 19e provides an image of Section A-A of the yaw joint of the strut structure of FIG. 16 provided in FIG. 19c.

DETAILED DESCRIPTION

The following description is merely exemplary in nature and is not intended to limit the present disclosure, application, or uses. Exemplary embodiments of the present teachings provide a unilateral external fixator device that allows for gross manipulation and fine adjustment of deformities in six degrees of freedom, allowing for a large mechanical advantage and adjustments of the fixator through a deformity correction process without disengaging the device from the patient.

FIG. 1 provides an image of a unilateral fixator 100 in accordance with an exemplary embodiment of the present teachings. Referring to FIG. 1, the fixator 100 comprises two compound movable joints 110, 120. Attached to each compound movable joint 110, 120 is a pin clamp 130, 140. The pin clamp can accept a variety of pins (not shown), which can be attached to bone fragments undergoing a deformity correction procedure. The compound movable joint 110 is attached to an extension strut 160. The compound movable joint 120 is attached to a base strut 150. The extension strut 160 may slide in and out of the base strut 150, thereby allow for a change in the distance between the two compound moveable joints 110, 120. FIG. 1 also indicates a section line A-A. Details of Section A-A are provided below, in connection with FIG. 2.

FIG. 2 provides an image 200 of Section A-A of the unilateral fixator provided in FIG. 1. Referring to FIG. 2, a base strut 220 forms the main structure of a strut assembly. An extension strut 210 is able to slide within the base strut 220. The extension strut 210 and base strut 220 are restrained from rotating relative to one another by a square key 230, which is inserted into a milled slot (not shown) in the base strut 220 and captured by a groove 350 (FIG. 3) in the extension strut 210. The extension of the extension strut 210 relative to the base strut 220 is affected through a linear adjuster 270. The linear adjuster 270 is captured within the base strut 220 by two snap rings 260. The linear adjuster 270 has threaded into it a threaded rod 240, whose other end is threaded into a solid threaded locking insert 250, such as a "KEENSERT" insert, which is in turn threaded into the extension strut 210. Once the threaded rod 240 is threaded into the linear adjuster 270, it is locked in place with a suitable thread locking compound. In an alternative embodiment, the threaded rod 240 could be made integral with the linear adjuster 270. The rotation of the linear adjuster 270 forces the threaded rod 240 to translate within the solid, threaded locking insert 250, which forces the extension strut 210 to translate within the base strut 220, thereby effecting extension or contraction of the strut assembly. The linear adjuster may be rotated by way of a knob adjuster or a tool, such as an alien wrench. One skilled in the art would appreciate that other mechanism may be employed to cause the extension strut 210 to move within the base strut 220 while ensuring that the base strut 220 and extension strut 210 may be locked into a fixed position when the exemplary fixator device of image 200 is positioned on a patient. Such a mechanism might resemble a turnbuckle that is engaged to a radial pin at either end that extends from both the base strut and extension strut, adjusting the length of the turnbuckle would thereby either extend of contract the extension strut relative to the base strut FIG. 3 provides an isomeric image 300 of an exemplary unilateral fixator provided in FIG. 1. Referring to FIG. 1 and FIG. 3, in this exemplary embodiment, a compound movable joint 110 is attached to the base strut 160 and a compound movable joint 120 is attached to the extension strut 150. These two compound movable joints 110, 120 are identical. The compound movable joints 110, 120 each include two revolute joints 302, 304, 306, 308, the axes of which are orthogonally opposed. In alternative embodiments, the axes could be at angles other then ninety degrees.

The compound movable joint 110, also referred to herein as the wrist, is able to rotate about, but not slide along, the axis of the extension strut 160. The compound movable joint 120, also referred to herein as the ankle, is able to slide along, but not rotate about, the axis of the base strut 150. Both the ankle 120 and the wrist 110 can be locked in place relative to their respective struts 150, 160 by tightening their corresponding cap screw 310. In this exemplary embodiment, the ankle 120 and wrist 110 include multiple cap screws 310 (some not shown) to fix a given component of one of the compound movable joints 110, 120 in a specific configuration. These cap screws 310 are preferably made of corrosion resistant steel (CRES, or stainless steel). One skilled in the art would appreciate that the exact size of the cap screws 310 used will vary with the specific application of the fixator. Similarly, the cap screws 310 may be made of other materials suitable for medical device applications.

In an alternative embodiment, the compound movable joint 110 could be made to slide along, but not rotate about, the axis of the extension strut 160. Similarly, the compound movable joint 120 could be made to rotate about, but not slide along, the axis of the base strut 150. Alternatively, the base strut 150 and the extension strut 160 could be made to rotate relative to one another and the compound movable joint 110 and compound movable joint 120 could be fixed to the extension strut 160 and the base strut 150, respectively.

Attached to each compound movable joint 110, 120 is a clamp plate 320 and a clamp body 330. These clamp plates 320 and clamp bodies 330 receive pins (not shown) or other suitable devices for attaching the compound moveable joints 110, 120 to a patient's body. These clamp plates 320 and clamp bodies 330 may be made from an aluminum alloy #2024 or other materials suitable for medical device applications. The clamp plate 320 is secured to the clamp body 330 with four cap screws 340. Each cap screw 340 may be threaded into a combination of holes such that cap screws 340 straddle each pin (not shown). In one exemplary embodiment, each pin (not shown), being cylindrical in form, would have around it two split balls (not shown) each of which is clamped in the grooves of the clamp plate 320 and the clamp body 330. The split balls (not shown) would have the ability to slide along the grooves to allow both divergent and convergent pin arrangements in a given plane.

FIG. 4a provides an alternative image of an exemplary unilateral fixator 500. FIG. 4b provides an image of Section B-B of the unilateral fixator provided in FIG. 4a. Referring to FIG. 4a and FIG. 4b, the image of the exemplary unilateral fixator 500 shows a B-B section line, cutting through the compound movable joint 120. In this exemplary embodiment, section B-B 401 depicts details common to both compound movable joints 110, 120. Also, the compound movable joints 110 and 120 each comprise two revolute joints 405, 410. As such, FIG. 4b depicts a cross section of each of the two revolute joints 405, 410, and specifically illustrates an exemplary gear reduction mechanism. To avoid clutter in FIG. 4b, items, although common to both revolute joints 405, 410, are identified once. One skilled in the art would appreciate that an item identified on one of the revolute joints is also present in the other.

Each revolute joint 405, 410 may include left-hand helical spline 460 includes a cylinder having an internal left hand helical spline. In line with the left-hand helical spline 460 is a right-hand helical spline 420, which is a cylinder having an internal right hand helical spline. Separating the left-hand helical spline 460 and the right-hand helical spline 420 is a thrust washer 445. Sliding within and rotationally engaged to both the left-hand helical spline 460 and the right-hand helical spline 420 is a helical spool 440. The helical spool 440 has both a left and a right external helical spline that has the same helix angle as does its mating parts. The left hand internal and external helical splines must have the same diametral pitch, number of teeth, and helix angle as one another and, similarly, the right hand internal and external helical splines must have the same diametral pitch, number of teeth, and helix angle as one another. However, these characteristics for the left hand helical splines could differ from these characteristics for the right hand helical splines.

The left-hand helical spline 460, the right-hand helical spline 420, and the thrust washer 445 are axially-clamped together using a cap screw 465, a thrust washer 470, a spacer 435, a castelated nut 450, and a roll pin 425. First, the thrust washer 470 and spacer 435 are fit over the cap screw 465. Then, the spacer 435 is fit into a counter bore in the left-hand helical spline 460. The helical spool 440 is then engaged with the left-hand helical spline 460 and the cap screw 465 is threaded into the helical spool 440 as it slides with the left-hand helical spline 460. The thrust washer 445 is then held against the left-hand helical spline 460 and the right-hand helical spline 420 is slid onto the helical spool 440 with the counter bore away until it comes up against the thrust washer 445. The spacer 435 is then fitted over the cap screw 465 and into the counter bore of the right-hand helical spline 420. Thrust washer 470 is then fitted over the cap screw 465 and the castelated nut 450 is threaded onto the cap screw 465 with a final preload applied to eliminate any lash from the assembly. The roll pin 425 is then pressed into a hole in the cap screw 465 and aligned to one of the slots in the castellated nut 450.

The helical spline gear reducer assembly, that is, the left-hand helical spline 460, the right-hand helical spline 420, the helical spool 440, the cap screw 465, and the other associated components described above, is then slipped within a split bore of a roll housing 415. The assembly is retained axially within the bore through the use of two cap screws 475, one of which clamps and locks the left-hand helical spline 460 and the other of which clamps and locks the right-hand helical spline 420.

Using two separate cap screws 475 allows for the locking of the ground reference and/or the output of the helical spline gear reducer assembly relative to the roll housing 415. Initially, both cap screws 475 would be in place but not tightened. This configuration would allow the free rotation of the helical spline gear reducer assembly and thus the output within the roll housing 415. Locking of the first cap screw 475 effectively prevents the rotation of the left-hand helical spline 460 relative to the roll housing 415. The right-hand helical spline 420 is then able to rotate only through the rotation of the cap screw 465. Locking of the second cap screw 475 effectively prevents the rotation of the right-hand helical spline relative to the roll housing 415. The reason for this second locking provision is twofold. First, in the event that no further adjustment is desired, or for added structural integrity, the revolute joint can be locked. Second, because of the limited length of the left-hand helical spline 460, the right-hand helical spline 420, and the helical spool 440, the output of the helical spline gear reducer operates within a limited rotation angle based on the reduction ratio. If the output rotation needs to be increased, the right-hand helical spline 420 can be locked while the left-hand helical spline 460 is unlocked. This configuration effectively allows the cap screw 465 to be backed off to reposition the helical spool 440 such that the output angulation range can be extended.

In an alternative embodiment, the separate cap screws 475 may be omitted. In this case, the helical spool 440 and the left-hand helical spline 460 and the right-hand helical spline 420 may have helical angles such that they are self-locking. The helical angles for the helical spool and the left-hand helical spline 460 and the right-hand helical spline 420 may be close to a threshold value for self-locking. This value will vary by material and size of the left-hand helical spline 460 and the right-hand helical spline 420, but may be in the range of 15 to 25 degrees. In this case, the cap screw 465 could be configured to be threaded into the helical spool 440 but not threaded or captured with the castellated nut 450. This configuration would allow the cap screw 465 and the helical spool 440 to move axially with the left hand helical spline 460 and the right hand helical spline 420 if the rotational and frictional forces are favorable. The castellated nut 450 and the roll pin 425 would be replaced with another form of axial restraint such as a snap ring that would be engaged when the cap screw 465 was threaded completely into the helical spool 440. Once the snap ring was engaged further axial translation of the helical spool 440 could only be accomplished through the rotation of the cap screw 465 which would allow for fine adjustment.

When the cap screw 465 is not engaged with the snap ring, i.e., when the helical spool 440 is not restrained axially, other than from friction between the helical teeth, from sliding within the left-hand helical spline 460 and the right-hand helical spline 420 and they are not further locked in place, the compound movable joint 410 could be subjected to an external stimulation, for example, a vibrational force could be applied to the compound movable joint 410. As such, this vibrational force could overcome the small frictional force that provides the self-locking capability of the helical spool 440 relative to the left-hand helical spline 460 and the right-hand helical spline 420. So, by applying and removing a vibrational force, or other force that can overcome the frictional forces between the helical spool 440 and the left-hand helical spline 460 and the right-hand helical spline 420 without adversely affecting the unilateral fixator's positioning on the patient, the revolute joints of the compound movable joint 410 could be instantly loosened and tighten without the need for tightening screws or similar mechanisms.

Once the helical gear reducer assembly is assembled within the roll housing 415, the pitch housing 430 is then threaded and torqued onto the right-hand helical spline and locked in place using a suitable bonding compound or mechanical retention device. In an alternative embodiment, this assembly could also be done prior to the insertion of the helical spline gear reducer assembly into the roll housing 415. The pitch housing 430 also has two cap screws 480 that function in the same way as those in the roll housing 415. In this exemplary embodiment, the pitch housing 430 operates the same in the revolute joint 410 as the roll housing 415 operates in the revolute joint 405.

The output end of the right-hand helical spline 420 contained in the revolute joint 410, which has been assembled into the pitch housing 430, is threaded onto it the clamp assembly consisting of a clamp plate (not shown), a clamp body 455, and four cap screws (not shown). The clamp body 455, having been threaded and torqued onto the right-hand helical spline 420, provides a stable base for one or more pins to be clamped between the clamp body 455 and the clamp plate (not shown).

Operation of the helical spline gear reducer assembly is fairly straightforward. If the left-hand helical spline 460 is considered the ground and the cap screw 465 is rotated counter clockwise, the helical spool 440 must move axially away from the head of the cap screw 465, since it is threaded onto the cap screw 465. Since the helical spool 440 is rotationally-engaged with the left-hand helical spline 460, the helical spool 440 must also rotate in a counter clockwise fashion in accordance with the left hand helix angle that is common to both the helical spool 440 and the left-hand helical spline 460. Since the helical spool 440 is also rotationally-engaged with the right-hand helical spline 420 as it is forced to translate and rotate within the left-hand helical spline 460 and along the cap screw 465, the right-hand helical spline 420 is forced to rotate counter clockwise due to the nature of the right hand helix that is common to both the helical spool 440 and the right-hand helical spline 420.

The net effect of this movement is based on the pitch of the thread on the cap screw 465 and the helix angles on the left-hand helical spline 460, the right-hand helical spline 420, and the helical spool 440. The effective reduction ratio may be rather large. This large effective reduction enables the gear reduction mechanism to be finely adjusted. This fine adjustment may be implemented when the unilateral fixator device is engaged with the bone fragments of a deformity. For simplicity in reading the position of one of the revolute joints 405, 410, it may be desirable to have three hundred and sixty, in other words, the number of degrees in a circle, be an integer multiple of the reduction ratio. For example, if the reduction ratio was seventy-two to one, a scale on the output having seventy-two graduations would allow a reading to the nearest five degrees, a scale on the input having fifty graduations would then allow for precise readings down to the tenth of a degree. Interpolation between the graduations on the input or the use of a vernier scale could obtain readings as precise as one one-hundredth of a degree, although this level of precision would be much less than the lash in the system and therefore not necessary. Still, the gear reduction mechanism of the present teachings allows for very fine adjustment of the fixator position through the cap screw 465, much finer than is seen in the prior art. Although the arrangement of this exemplary embodiment is an axial construction, one skilled in the art would appreciate that a concentric arrangement would work as well, although this alternative configuration might be more difficult to construct.

FIG. 5 provides an image of Detail A 500 of the unilateral fixator provided in FIG. 2. FIG. 6 provides an image of Section C-C 600 of Detail A of FIG. 3 showing a gear assembly for the unilateral fixator in accordance with an exemplary embodiment of the present teachings. Referring to FIG. 4b, FIG. 5 and FIG. 6, an upper revolute joint 405, that is, the one revolute joint of the two revolute joints 405, 410 that comprise a compound movable joint that is attached to the strut assembly, can rotate about the strut assembly of an exemplary fixator. To effect this rotation, ring gear 540 is bonded to a counter bore in an upper portion of the roll housing 415. A spur gear 610 having two slots, one on either face that are orthogonally opposed, is slideably-engaged to one half of an Oldham disk 530, which consists of a disk having two rectangular-in-section teeth orthogonally opposed on either face. The Oldham disk 530 is then slideably-engaged into a slot in the face of the extension strut 160 (FIG. 1). On top of the spur gear 610 is another Oldham disk 530, which is slideably-engaged to the slot in the spur gear 610. A spin dial 550 is then slideably-engaged to the other side of the Oldham disk 530 and centered on the outer diameter of the ring gear 540. The spin scale 520 indicates the shaft assembly rotation as observed from the upper end of the device. The spin dial 550 is then slipped into the bore of the spur gear 610. Since the outer diameter of the boss on the spin dial 550 is eccentric to a degree twice of which is the difference of the pitch diameters of the ring gear 540 and the spur gear 610, the spin dial 550 forces the spur gear 610 to engage the ring gear 540. Rotation of the spin dial 550 forces each successive tooth on the spur gear 610 to engage with each successive tooth on the ring gear 540. The resulting ratio is the difference in the number of teeth between the ring gear 540 and the spur gear 610 divided into the number of teeth on the ring gear 540. Like with the helical spline gear reducer it is desired to have three hundred and sixty, i.e., the number of degrees in a circle, be an integer multiple of the reduction ratio.

The discussion above, in connection with FIGS. 4a, 4b, 5 and 6, describe a gear reduction mechanism of a revolute joint. One skilled in the art would appreciate that an alternative embodiment may employ a different mechanism. For example, an alternative embodiment may include a pair of roller bearing assemblies in either a face-to-face or a back-to-back arrangement depending on the moment stiffness required, and they serve to allow one revolute joint to rotate about another revolute joint that is connected to it. The roller bearing assemblies in this alternative embodiment are tapered roller bearings, such bearings are often use in wheel bearing assemblies for automobiles and are well suited for applications requiring a high degree of moment stiffness. One skilled in the art would appreciate that other types of roller bearings assemblies could be used, such as a simple angular contact ball bearing in either a preloaded double or duplex arrangement. Additionally, for lower cost and performance, plain bearings could be used.

In this alternative exemplary embodiment, each of the five revolute joints also houses a worm gear in a bore that is normal to and offset from that which houses the roller bearing assemblies. The worm gear is held in place with two snap rings. Stacked on top of the bearing assemblies is a gear having the same axis of revolution as the roller bearing assemblies.

In this alternative exemplary embodiment, a gear contained in each of the five revolute joints has a face spline on the external face that mates with another face spline on a lock bushing. The lock bushing has a cylindrical spline on the inner diameter that engages with a cylindrical spline on the shaft of a revolute joint. A lock nut threads onto the shaft of the revolute joint and clamps the lock nut, gear, and roller bearing assemblies to the body of the revolute joint. Tightening the lock nut locks the face splines of the gear and the lock nut together. Since the lock nut has a cylindrical spline that is always engaged with a cylindrical spline on the shaft of the revolute joint, tightening the lock nut essentially locks the gear to the shaft of the revolute joint. The gear and lock nut combination contained in each revolute joint enables each joint to be separately locked in a similar manner.

In the locked condition, turning the worm gear that is always meshed with the gear controls the angulation of the associated revolute joint. This alternative exemplary embodiment uses an alien head connected to the worm gear to turn the worm gear, using an alien key. The mesh between worm gear and gear is self-locking and cannot be back driven, so a lock is not necessary in this embodiment. However if a lock is desired, a spring-loaded detent-style lock can be added. In the loose condition, the lock nut allows the gear and lock nut to rotate relative to one another. This freedom to rotate allows for the rapid, gross, manipulation of the associated joint to get the device mounted and to reduce the gross deformity of the bone in a single step if desired.

In this alternative embodiment, a compound movable joint is capable of sliding along a strut assembly houses either an additional worm gear or similar threaded adjuster. The strut passes through the body of this sliding joint. The worm gear or threaded adjuster allows for the linear height adjustment of the sliding joint. In one alternative embodiment, this linear adjustment is comprised of a rack captured in an extruded aluminum tube. It uses a dovetail type construction to capture it and a screw to keep it from sliding along the length of the strut. For anti-rotation, two guide rails are used. These guide rails also are captured using a dovetail type configuration. Two shoes are then inserted into the revolute joint that moves along the strut to allow the joint to slide along the guide rails to provide anti-rotation and to take up lash. The sliding joint also includes a locking clamp or nut to prevent gross movement of the slider. When unlocked, the sliding joint can be rapidly adjusted. Once locked, it includes an allen nut attached to a worm gear, similar to the worm gear used in the five revolute joints and described above, that allows fine adjustment of the sliding joint along the rack. One skilled in the art would appreciate that a variety of sliding mechanisms could be used in addition to the rack and pinion configuration of this exemplary embodiment.

FIG. 7 provides an image of a compound movable joint 700 in accordance with an exemplary embodiment of the present teachings. Referring to FIG. 7, the compound movable joint 700 comprises two revolute joints 710, 720. Each revolute joint 710, 720 may have a scale 730, 740 integral with the mechanism to accurately establish the needed configuration for the fixator. The roll housing 750 and pitch housing 760 may be tightened around helical spline assemblies (not shown) using cap screws 770 and cap screws 780, respectively.

FIG. 8a provides a front image 805 of a unilateral fixator in accordance with an alternative exemplary embodiment of the present teachings. FIG. 8b provides a side image 810 of a unilateral fixator in accordance with an alternative exemplary embodiment of the present teachings. FIG. 8c provides a top image 815 of a unilateral fixator in accordance with an alternative exemplary embodiment of the present teachings. FIG. 9 provides an isomeric image 900 of a unilateral fixator in accordance with an alternative exemplary embodiment of the present teachings. Referring to FIGS. 8a, 8b, 8c, and 9, in this embodiment, the present teachings comprise two movable joints 820, 830, connected by a single strut 840. Each movable joint has two revolute joint segments 850, 860, with one movable joint 820 being able to be slide along the body of the strut 840. Each movable joint 820, 830 is then clamped to the strut 840. The strut 840 allows for both linear motion, by an inner segment of strut 840 moving within an outer segment of strut 840, as well as rotational motion between the ends where the movable joints 820, 830 are attached. The two movable joints 820, 830 allow for rotation movement in two orthogonally opposed degrees of freedom. Taken together the movable joints 820, 830 and the strut 840 allow for motion in all six degrees of freedom.

FIGS. 10a-10c provide a front image 1005, a side image 1010, and a top image 1015, respectively, of a compound movable joint in accordance with an alternative exemplary embodiment of the present teachings. FIG. 11 provides an isomeric image 1100 of a compound movable joint in accordance with the alternative exemplary embodiment of the present teachings illustrated in FIGS. 11a-10c. Referring to FIGS. 10a, 10b, 10c, and 11, in this embodiment, the compound movable joint 1005, 1010, 1015, 1020, 1100 is comprised of two revolute joints 1070, 1080 and a clamp assembly 1060. The first revolute joint, also referred to herein as a roll joint 1070 provides revolute motion between the limits of plus or minus ninety degrees about an axis orthogonal to the main axis of the strut structure 840 (FIG. 8). The second revolute joint, also referred to herein as a pitch joint 1080 is directly fixed to the output of the roll joint 1070 and as such follows the revolute motion of the roll joint 1070. The pitch joint 1080 provides revolute motion between the limits of plus or minus sixty degrees about an axis orthogonal to the output axis of the roll joint 1070. The pitch joint 1080 and roll joint 1070 are fixed to one another through the use of a roll-pin 1050. A clamp assembly 1060 is attached to the output of the pitch joint 1080 through the use of a woodruff key, shown in detail in the cross section of the clamp assembly, FIG. 15e.

FIG. 12a provides a front image of the first of two revolute joints 1210, the roll joint, of a compound movable joint in accordance with an alternative exemplary embodiment of the present teachings. FIGS. 12b-12d provide a side image 1220, a top image 1230, and an isomeric image 1240 of same revolute joints. FIG. 12e provides an image of Section A-A 1250 of the first of two revolute joints of a compound movable joint provided in FIG. 12c. FIG. 12f provides an image of Section B-B 1270 of the first of two revolute joints of a compound movable joint provided in FIG. 12b. FIG. 12g provides an image of Section C-C 1280 of the first of two revolute joints of a compound movable joint provided in FIG. 12b. FIG. 12h provides an image of Section D-D 1290 of the first of two revolute joints of a compound movable joint provided in FIG. 12b. Referring to FIGS. 12a through 12h, Section A-A presents a view of a housing 1257, which provides the structural support of the roll joint 1210, 1220, 1230, 1240 and houses all of the internal components of the roll joint 1210, 1220, 1230, 1240. Screw 1256 provides a clamping load on the strut 840 (FIG. 8a) which the roll joint 1210, 1220, 1230, 1240 is slipped over and is used to lock the position of the roll joint 1210, 1220, 1230, 1240 relative to the strut 840 (FIG. 8a). The remaining mechanism is used to provide fine adjustment of the roll joint 1210, 1220, 1230, 1240.

A plain bearing 1259 supports a drive shaft 1258 in the housing 1257. Coupled to the drive shaft 1258 is an Oldham disk 1255. The Oldham disk 1255 is slideably-engaged to the drive shaft 1258 using a tongue protruding from the plane of the disk and a slot in the drive shaft 1258. Coupled to the other side of the Oldham disk 1255 is a gear 1253, which, like the drive shaft 1258, has a slot that engages a tongue protruding from the plane of the Oldham disk 1255. This arrangement efficiently transmits torque between the gear 1253 and the drive shaft 1258 while allowing for radial misalignment. The gear 1253 has its radial alignment controlled by a cam 1251, which is of circular cross section having an axis that is eccentric from the axis of rotation, which is defined by the circular protrusion that is within a knob adjuster 1254 interfacing with the tree pan of the cam 1251. This circular protrusion is itself eccentric to the tree pan of the knob adjuster 34, which controls the axis of rotation of the knob adjuster 1254 with respect to the housing 1257. The cam 1251 is affixed to the lock knob 1252, which, when rotated, causes the cam 1251 to rotate. The degree to which the outer diameter of the cam 1251 is eccentric with respect to the tree pan of the cam 1251 is the same as the degree to which the inner protrusion of the knob adjuster 1254 is eccentric to the tree pan of the knob adjuster 1254. This identity allows the eccentricity of the cam 1251 to either cancel out the eccentricity of the knob adjuster 1254, making the gear 1253 concentric with the housing 1257, or acts to double the degree of eccentricity the cam 1251 has with respect to the housing 1257, making the gear 1253 come in contact with the housing 1257.

The housing 1257 has internal gear teeth having the same pitch as the external gear teeth of the gear 1253 although the number of teeth on the housing 1257 exceeds that on the gear 1253 by a small fraction of the total number of teeth on the housing 1257. This small difference in the number of teeth does two things. One, the difference allows for clearance such that the gear teeth mesh on the side of contact and that they clear on the side of clearance. Two, by dividing the difference in the number of teeth into the total number of teeth on the housing 1257, the result is a gear reduction ratio. This type of gear reduction is known as cycloidal reduction.

FIG. 12f shows a cross section B-B of the gear mesh and shows the degree of eccentricity. Similarly, the same type of reduction can be achieved using a device called a harmonic drive where the inner gear is a flexible member that is deformed into an elliptical shape using an elliptical bearing or two bearings centered on the two foci of the ellipse, which has gear teeth meshing on the major axis of the ellipse and clearance on the minor axis of the ellipse.

To provide a detent lock to the knob adjuster 1254 a ball detent is used. FIG. 12g depicts section C-C. The knob adjuster 1254 in the area of the ball detent has a knurling around the inner diameter of the tree pan. This knurling engages a steel ball 1261 that is spring loaded outward through the compression of an elastomeric ball 1260, both of which lie in a radial flat bottomed hole. Rotation of the knob adjuster 1254 causes compression of the elastomeric ball 1260 to disengage the steel ball 1261 from the knurling of the knob adjuster 1254.

Referring to FIG. 12h, which depicts section D-D, the knob adjuster 1254 is secured to the housing 1257 using a square section wire 1262 that is inserted through holes in the knob adjuster 1254 that come off on a tangent to the inner tree pan. The wire 1262 follows a groove in the wall of the tree pan of the knob adjuster 1254 as well as a groove in the wall of the housing 1257. One skilled in the art would appreciate that other methods of securing the know adjuster 1254 to the housing 1257, such as snap rings or swaging methods could also be used.

The mechanical operation of the roll joint 1210, 1220, 1230, 1240 described above in connection with FIGS. 12a through 12h, is identical to the three other revolute joints that comprise this alternative embodiment, as illustrated in FIGS. 8a, 8b, and 8c.

FIG. 13 provides a perspective view of the drive mechanism of the first of two revolute joints of the movable joint structure in accordance with an exemplary embodiment of the present teachings. A knob adjuster 1310 is connected to a drive shaft 1330 through an Oldham disk 1320. The Oldham disk 1320 is slideably-engaged to the drive shaft 1330 using a tongue protruding from the plane of the disk and a slot in the drive shaft 1330. This coupling arrangement is accomplished through the tongues protruding from either side of the plane of the Oldham disk 1320, which are orthogonal to each other.

FIG. 14a provides a front image of the second of two revolute joints 1410, the pitch joint, of a compound movable joint in accordance with an alternative exemplary embodiment of the present teachings. FIG. 14b provides a side image of the second of two revolute joints 1420 of a compound movable joint in accordance with an alternative exemplary embodiment of the present teachings. FIG. 14c provides a top image of the second of two revolute joints 1430 of a compound movable joint in accordance with an alternative exemplary embodiment of the present teachings. FIG. 14d provides an isomeric image of the second of two revolute joints 1440 of a compound movable joint in accordance with an alternative exemplary embodiment of the present teachings.

FIG. 14e provides an image of Section A-A 1450 of the second of two revolute joints of the compound movable joint provided in FIG. 14c.

Referring to FIGS. 14a through 14e, section A-A presents a view of a housing 1455, which provides structural support of the pitch joint 1410, 1420, 1430, 1440, 1450 and houses all of the internal components of the pitch joint 1410, 1420, 1430, 1440, 1450. Screws 1460, 1465 provide a clamping load in two areas; the first is to clamp on the output boss of the roll joint (not shown) to prevent rotation of the pitch joint 1410, 1420, 1430, 1440, 1450 relative to the roll joint (not shown). This clamping action is meant to provide a safety lock and to ensure that the pitch joint 1410, 1420, 1430, 1440, 1450 does not move by back driving the gear reduction mechanism under shock or heaving load. The second clamp screw clamps a drive shaft 1470 of the pitch joint 1410, 1420, 1430, 1440, 1450 to the housing 1455 of the pitch joint 1410, 1420, 1430, 1440, 1450. This clamping action was done for the same reason as the first clamping action of the screw, specifically to prevent rotation of the clamp assembly relative to the pitch joint 1410, 1420, 1430, 1440, 1450. The drive shaft 1470 is supported in the housing 1455 with two plain bearings 1475, 1480. All other aspects of the pitch joint 1410, 1420, 1430, 1440, 1450 are the same as the aspects described for the roll joint in connection with FIGS. 12a through 12h.

FIG. 15a provides a front image of a pin clap unit 1510 in accordance with an exemplary embodiment of the present teachings. FIG. 15b provides a side image of a pin clap unit 1520 in accordance with an exemplary embodiment of the present teachings. FIG. 15c provides a top image of a pin clap unit 1530 in accordance with an exemplary embodiment of the present teachings. FIG. 15d provides an isomeric image of a pin clap unit 1540 in accordance with an exemplary embodiment of the present teachings. FIG. 15e provides an image of Section A-A of the pin clap unit 1550 provided in FIG. 15c.

Referring to FIGS. 15a through 15e, a housing 1555 provides the structural support of the pin clamp 1510, 1520, 1530, 1540, 1550 and interfaces with the drive shaft 1470 (FIG. 14e) through the use of a Woodruff key, the slot 1585 for which is contained in the housing 1550. Two clamp sleds 1570 are captured in the housing 1555 through the use of a dovetail configuration. The clamp sleds 1570 are preloaded to the ends of the dovetail slot with a spring 1575 and are prevented from sliding out of the dovetail groove by two roll pins 1565. Two cleats 1580, one having a right hand threaded bore and the other having a left hand threaded bore, lie in a cut beneath the dovetail grove the upper end of each extending beyond the cut into the dove tail groove. The spring 1575 is captured by a small circular boss on each clamp sled 1570 that fits within the inner diameter of the spring 1575. A threaded rod 1560 having a right hand male thread on one end and a left hand male thread on the other is located in a transverse bore in the housing 1555 and is threaded into the cleats 1580. A hex or square head may be on each end of the threaded rod 1560 such that when rotated the cleats 1580 either move toward the center of the rod or towards it ends. In so doing, the cleats 1580 make contact with the clamp sleds as the cleats move outward, clamping pins (not shown) between the clamp sleds 1570 and the housing 1555. When the cleats 1580 are moves toward the center of the threaded rod 1560, the spring 1575 provides the clamping force. The spring 1575 allows the pins (not shown) to be snapped into place as the clamp sleds 1570 and the housing 1555 have chamfered edges as a lead into the clamping cavity. The spring 1575 will hold the pins in place while the device is positioned, rotating the threaded rod 1560 such that the cleats 1580 move outward and positively clamp the pins to the housing 1555. One skilled in the art would appreciate that this clamp configuration is one example of many possible clamp types that can be used with a unilateral fixator of the present teachings.

FIG. 16a provides a front image of a strut structure 1610 in accordance with an alternative exemplary embodiment of the present teachings. FIG. 16b provides a side image of a strut structure 1620 in accordance with an alternative exemplary embodiment of the present teachings. FIG. 16c provides a top image of a strut structure 1630 in accordance with an alternative exemplary embodiment of the present teachings. FIG. 16d provides an isomeric image of a strut structure 1640 in accordance with an alternative exemplary embodiment of the present teachings. Referring to FIGS. 16a through 16d, the strut structure 1610, 1620, 1630, 1640 is comprised of three components, a main body 1650, which accepts a top tube 1660 and provides for the linear adjustment of the top tube 1660 relative to the main body 1650. The top tube 1650 accepts a yaw joint 1670, which allows for rotation of the yaw joint 1670 relative to the combined main body 1650 and top tube 1660.

FIG. 17a provides a front image of a base tube assembly 1710 in accordance with an alternative exemplary embodiment of the present teachings. FIG. 17b provides a side image of a base tube assembly 1720 in accordance with an alternative exemplary embodiment of the present teachings. FIG. 17c provides a bottom image of a base tube assembly 1730 in accordance with an alternative exemplary embodiment of the present teachings. FIG. 17d provides an isomeric image of a base tube assembly 1740 in accordance with an alternative exemplary embodiment of the present teachings. FIG. 17e provides an image of Section A-A of the base tube assembly 1750 provided in FIG. 17c.

Referring to FIGS. 17a through 17e, screw adjuster 1790 is retained within a strut housing 1760 through the use of a retaining ring 1780. An O-ring 1770 seats in a circumferential groove around the inner diameter of the strut housing 1760 and squeezes the outer diameter of the screw adjuster 1790 providing friction to keep the screw adjuster 1790 from being back driven or from rotation under shock and vibration.

FIG. 18a provides a front image of a top tube assembly 1810 in accordance with an alternative exemplary embodiment of the present teachings. FIG. 18b provides a side image of a top tube assembly 1820 in accordance with an exemplary alternative exemplary of the present teachings. FIG. 18c provides a top image of a top tube assembly 1830 in accordance with an alternative exemplary embodiment of the present teachings. FIG. 18d provides an isomeric image of a top tube assembly 1840 in accordance with an alternative exemplary embodiment of the present teachings.

Referring to FIGS. 18a through 18d, top tube housing 1850 provides the main structural support for the top tube 1810, 1820, 1830, 1840. Attached to top tube 1810, 1820, 1830, 1840 is guide rail 1890, which has a graduated scale to read off elongation and it also serves to prevent rotation of the top tube 1810, 1820, 1830, 1840 relative to the top tube housing 1850. The guide rail 1890 slides into a dovetail groove in the top tube housing 1850 and itself has a dovetail shape for a cross section and a roll pin 1880 for retention. At the top of the top tube housing 1850 is a bore 1845 that receives the yaw joint (not shown). Within the bore 1845 is a keyway 1895 such that the drive shaft of the yaw joint (not shown) is fixed from a rotational standpoint to the top tube housing 1850. To lock up the yaw joint (not shown), a clamp screw 1870 is used in conjunction with two clamp bushings 1860, one being threaded and the other having a clearance hole. Tightening the clamp screw 1870 locks the rotation of the top tube housing 1850.

FIG. 19a provides a front image of the yaw joint 1910 of the strut structure of FIG. 16. in accordance with an alternative exemplary embodiment of the present teachings. FIG. 19b provides a side image of the yaw joint 1920 of the strut structure of FIG. 16. in accordance with an alternative exemplary embodiment of the present teachings. FIG. 19c provides a bottom image of the yaw joint 1930 of the strut structure of FIG. 16. in accordance with an alternative exemplary embodiment of the present teachings. FIG. 19d provides an isomeric image of the yaw joint 1940 of the strut structure of FIG. 16 in accordance with an alternative exemplary embodiment of the present teachings. FIG. 19e provides an image of Section A-A of the yaw joint 1950 of the strut structure of FIG. 16. provided in FIG. 19c.

Referring to FIGS. 18d and 19a through 19e, a Woodruff key 1960 engages the slot in the top tube housing 1850. The drive shaft 1970 is supported in the bore 1845 at the top end of the top tube 1840. The yaw joint housing 1965 provides the main structural support and houses all of the components of the yaw joint 1910, 1920, 1930, 1940, 1950 and provides the upper movable joint (not shown) a mount point around the outer diameter of the yaw joint housing 1965. The operation and mechanical description of the yaw joint is identical to the roll joint described in above, in connection with FIGS. 12a through 12h.

One skilled in the art would appreciate that the components of the exemplary unilateral fixators can be fabricated from corrosion resistant steel (CRES, or stainless steel), aluminum allows, brass, or other materials typically used for medical devices.

One skilled in the art would appreciate that the present teachings support a unilateral external fixator device that allows for gross manipulation and fine adjustment of deformities in six degrees of freedom. The device may comprise a strut assembly and two compound movable joints, one at each end of the strut assembly. One compound movable joint may comprise two revolute joints, each containing a gear reduction mechanism and may rotate about the strut. The other compound movable joint may contain two revolute joints, each containing a gear reduction mechanism, and may move along the length of the strut assembly. The gear reduction mechanisms may comprise helical spline assemblies that allow for gross and fine adjustment of the fixator.

What is claimed is:

1. A unilateral fixator for adjustment of a first bone portion relative to a second bone portion, the fixator comprising:
   a strut having first and second ends and a longitudinal strut axis, the strut telescopically adjustable along the strut axis;
   a first compound movable joint coupled to the first end of the strut and to a first bone attachment device, the first compound movable joint including a first gear mechanism, the first gear mechanism operable to control linear and rotational motion of the first bone attachment device relative to first and second axes while the first bone attachment device is engaged with the first bone portion, the first and second axes generally orthogonal to one another and to the strut axis; and
   a second compound movable joint coupled to the second end of the strut and to a second bone attachment device, the second compound movable joint including a second gear mechanism, the second gear mechanism operable to control linear and rotational adjustment of the second bone attachment device while the second bone attachment device is engaged to the second bone portion,
   wherein the first compound movable joint is rotatable about the strut axis.

2. The fixator of claim 1, wherein the strut includes first and second telescopically coupled members.

3. The fixator of claim 2, wherein the strut includes a key operable to control relative rotation between the first and second members.

4. The fixator of claim 1, wherein the strut includes a linear actuator operable to control linear adjustment of the strut along the strut axis.

5. The fixator of claim 1, wherein the first gear mechanism includes a first pair of helical splines separated by a thrust washer.

6. The fixator of claim 5, wherein the first gear mechanism includes a first cap screw axially clamping the first pair of helical splines and allowing linear and rotational adjustment about the first axis.

7. The fixator of claim 6, wherein the first gear mechanism includes a second pair of helical splines and a second cap screw allowing linear and rotational adjustment about the second axis.

8. The fixator of claim 6, wherein the first gear mechanism includes a thrust washer between the first pair of helical splines.

9. The fixator of claim 8, wherein the first gear mechanism includes a helical spool sliding within and rotationally engaged to each of the first pair of splines.

10. The fixator of claim 8, wherein the first pair of splines includes a left-hand helical spline and a right-hand helical spline.

11. The fixator of claim 1, wherein the first gear mechanism includes a spur gear coupled to an Oldham disk, and a ring gear.

12. The fixator of claim 11, wherein the first gear mechanism includes a spin dial engaged with the Oldham disk, and a spin scale.

13. The fixator of claim 1, wherein the second compound movable joint is rotatable about the strut axis.

14. The fixator of claim 1, wherein the second compound movable joint is slidable relative to the strut axis.

15. A unilateral fixator for adjustment of a first bone portion relative to a second bone portion, the fixator comprising:
   a strut having a longitudinal strut axis and first and second ends, the strut having adjustable length along the strut axis;
   a first revolute joint defining a first revolute axis generally orthogonal to the strut axis, the first revolute joint coupled to the first end of the strut;
   a second revolute joint defining a second revolute axis generally orthogonal to the first revolute axis and to the strut axis, the second revolute joint coupled the first revolute joint and to a first bone attachment device;
   a third revolute joint coupled to the second end of the strut and defining a third revolute axis generally parallel to the first revolute axis; and
   a fourth revolute joint coupled to the third revolute joint and to a second bone attachment device, the fourth revolute joint defining a fourth revolute axis generally parallel to the second revolute axis,
   wherein each of the first, second, third and fourth revolute joints includes a corresponding gear mechanism operable to adjust rotational and linear motion about the respective first, second, third and fourth revolute axes while the first and second bone attachment devices are engaged to the first and second bone portions.

16. The fixator of claim 15, wherein the first revolute joint is rotatably coupled to the strut and the third revolute joint is slidably coupled to the strut.

17. The fixator of claim 15, wherein the strut includes first and second strut members, the first strut member slidably coupled to the second strut member.

18. The fixator of claim 17, further comprising a key preventing relative rotation between the first and second strut members.

19. The fixator of claim 17, wherein the first and second strut members are rotatably coupled.

20. A unilateral fixator for adjustment of a first bone portion relative to a second bone portion, the fixator comprising:
 a strut having a longitudinal strut axis and first and second ends, the strut having adjustable length along the strut axis;
 a first compound movable joint coupled to the first end of the strut, the first compound movable joint coupled to a first clamp engageable with the first bone portion, the first compound movable joint including a first gear mechanism operable to control rotation and translation about first and second axes generally orthogonal to one another and to the strut axis; and
 a second compound movable joint coupled to the second end of the strut, the second compound movable joint coupled to a second clamp engageable with the second bone portion, the second compound movable joint including a second gear mechanism operable to control rotation and translation about third and fourth axes respectively generally parallel to the first and second axes,
 wherein the first compound movable joint is rotatable about the strut axis, and the second compound movable joints is slidable relative to the strut axis.

21. The fixator of claim 20, wherein first gear mechanism includes first and second gear devices, each of the first and second gear devices operable to control rotation and translation respectively about the first and second axes.

22. The fixator of claim 21, wherein the second gear mechanism includes third and fourth gear devices, each of the third and fourth gear devices operable to control rotation and translation respectively about the third and fourth axes.

23. The fixator of claim 20, wherein the first, second, third and fourth axes are offset from the strut axis.

* * * * *